(12) United States Patent
Song et al.

(10) Patent No.: US 9,494,669 B2
(45) Date of Patent: Nov. 15, 2016

(54) DIAGNOSIS OF CENTRAL NERVOUS SYSTEM WHITE MATTER PATHOLOGY USING DIFFUSION MRI

(75) Inventors: Sheng-Kwei Song, Manchester, MO (US); Qing Wang, St. Louis, MO (US); Yong Wang, St. Louis, MO (US)

(73) Assignee: Washington University, St. Louis, MO (US)

( * ) Notice: Subject to any disclaimer, the term of this patent is extended or adjusted under 35 U.S.C. 154(b) by 566 days.

(21) Appl. No.: 13/109,986

(22) Filed: May 17, 2011

(65) Prior Publication Data

US 2011/0282183 A1 Nov. 17, 2011

Related U.S. Application Data

(60) Provisional application No. 61/345,367, filed on May 17, 2010.

(51) Int. Cl.
*A61B 5/055* (2006.01)
*G01R 33/563* (2006.01)

(52) U.S. Cl.
CPC .............................. *G01R 33/56341* (2013.01)

(58) Field of Classification Search
CPC ............................................... G01R 33/56341
USPC .......................................................... 600/410
See application file for complete search history.

(56) References Cited

U.S. PATENT DOCUMENTS

| | | |
|---|---|---|
| 6,992,484 B2 | 1/2006 | Frank |
| 7,355,403 B2 | 4/2008 | Chakraborty |
| 2002/0042569 A1* | 4/2002 | Wedeen .................. 600/411 |
| 2005/0068031 A1* | 3/2005 | Frank ............... G01R 33/56341 324/309 |
| 2007/0217664 A1 | 9/2007 | Flipo et al. |
| 2008/0252291 A1* | 10/2008 | Hoogenraad et al. ........ 324/309 |

(Continued)

FOREIGN PATENT DOCUMENTS

WO WO 2010/017524 * 2/2010 ............. A61B 8/055

OTHER PUBLICATIONS

Descoteaux et al., "Mapping neuronal fiber crossings in the human brain", 2008, 3 pages.

(Continued)

*Primary Examiner* — Patricia Park
(74) *Attorney, Agent, or Firm* — Armstrong Teasdale LLP

(57) ABSTRACT

Determining diffusivity of multiple diffusion components within a tissue using diffusion magnetic resonance data representing a volume of the tissue. A plurality of candidate fibers having a direction is defined within the volume. A possibility coefficient is calculated by a processor for each candidate fiber of the plurality of candidate fibers based on the magnetic resonance data and the direction of the candidate fiber. The possibility coefficient represents a likelihood that the candidate fiber exists in the volume. Candidate fibers associated with a possibility coefficient greater than a threshold value are selected by the processor to create one or more probable fibers. For each probable fiber of the one or more probable fibers, an axial diffusivity indicating a diffusion of water in the direction of the probable fiber and a radial diffusivity indicating a diffusion of water perpendicular to the direction of the probable fiber are calculated by the processor. The diffusivity of isotropic diffusion component and the volume ratios of each fiber component and isotropic components are calculated.

14 Claims, 48 Drawing Sheets

(56) References Cited

U.S. PATENT DOCUMENTS

2009/0010517 A1* 1/2009 Basser et al. ............... 382/131
2009/0312625 A1* 12/2009 Du ............................. 600/410

OTHER PUBLICATIONS

Hagmann et al., "Mapping the Structural Core of Human Cerebral Cortex", PLOS Biology, 2008, pp. 1479-1493, vol. 6, Issue 7.
Nosey et al., "Inference of Multiple Fiber Orientations in High Angular Resolution Diffusion Imaging", Magnetic Resonance in Medicine, 2005, pp. 1480-1489, vol. 54.
Kim et al., "Quantification of Diffusivities of the Human Cervical Spinal Cord Using a 2D Single-Shot Interleaved Multisection Inner Volume Diffusion-Weighted Echo-Planar Imaging Technique", American Journal of Neuroradiology, 2010, 6 pages.
Ramirez-Manzanares et al., "Diffusion Basis Functions Decomposition for Estimating White Matter Intravoxel Fiber Geometry", IEEE Transactions on Medical Imaging, 2007, pp. 1091-1102; vol. 26, No. 8.
Song et al., "Increased radial diffusivity: A demyelination marker", Proc. Intl. Soc. Mag. Reson. Med., 2004, p. 723, vol. 11.

* cited by examiner

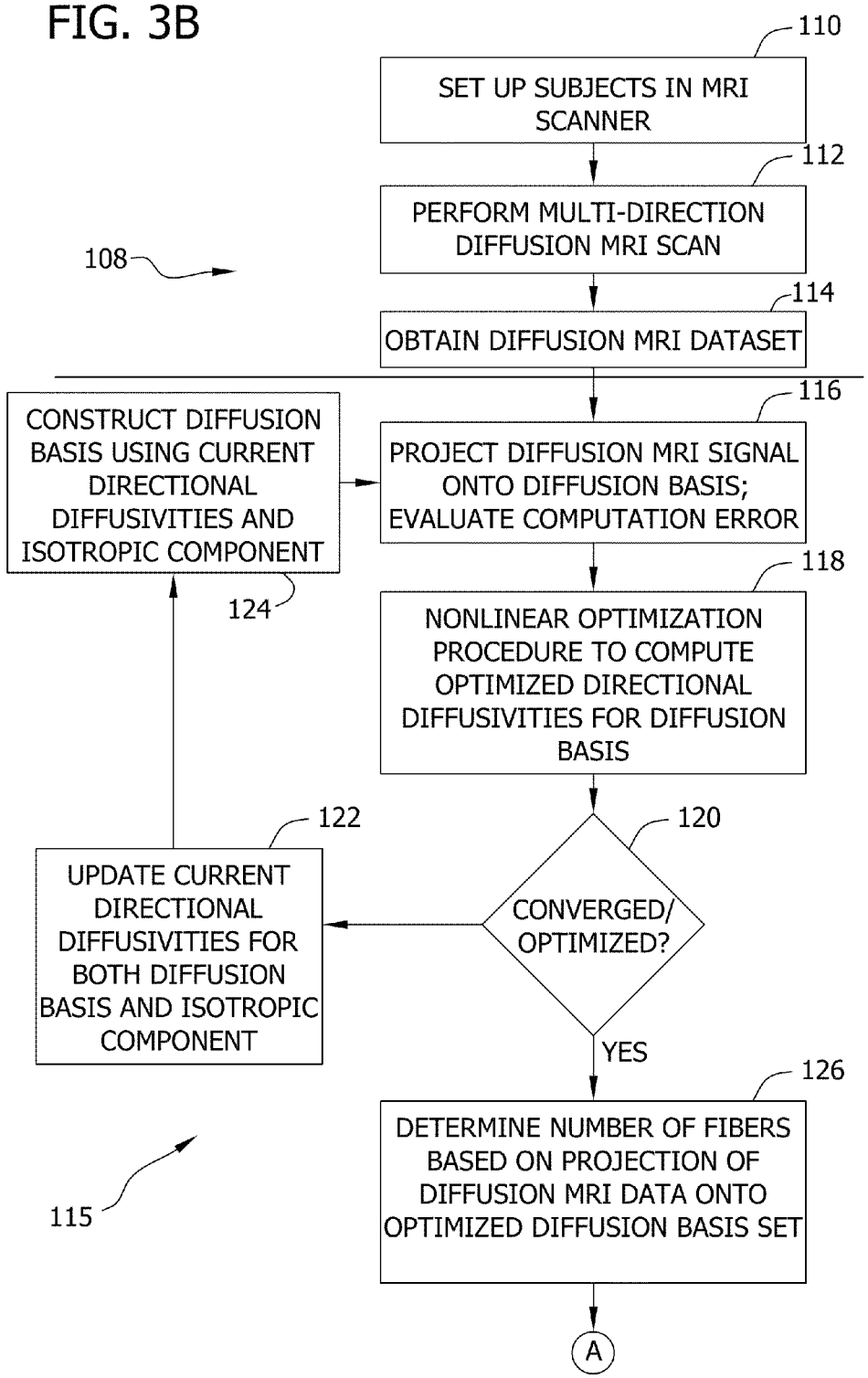

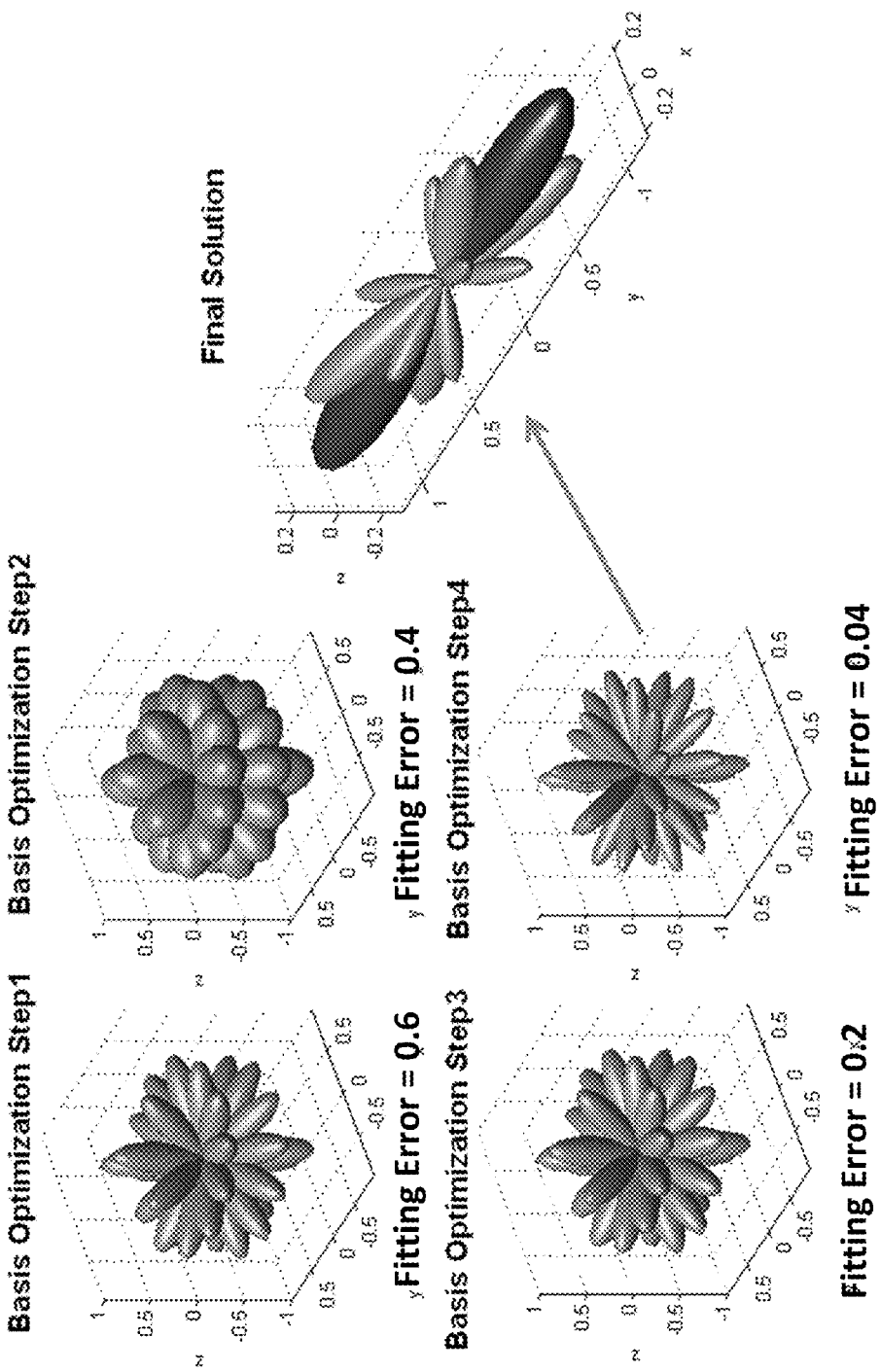

MBP

SMI-31

DAPI

WATER ing US 9,494,669 B2

DIAGNOSIS OF CENTRAL NERVOUS SYSTEM WHITE MATTER PATHOLOGY USING DIFFUSION MRI

CROSS REFERENCE TO RELATED APPLICATIONS

This application claims the benefit of U.S. Provisional Patent Application Ser. No. 61/345,367 entitled DIAGNOSIS OF CENTRAL NERVOUS SYSTEM WHITE MATTER PATHOLOGY USING DIFFUSION MRI filed on May 17, 2010, the entirety of which is hereby incorporated by reference.

STATEMENT REGARDING FEDERALLY SPONSORED RESEARCH & DEVELOPMENT

This invention was made with government support under grants R01-NS047592, R01-NS054194, and P01-NS059560, awarded by the U.S. National Institutes of Health. The government has certain rights in the invention.

BACKGROUND

Aspects of the disclosure relate generally to magnetic resonance imaging (MRI) and, more particularly, to diffusion magnetic resonance data provided by an MRI scanner.

White matter injury is common in central nervous system (CNS) disorders and plays an important role in neurological dysfunctions in patients. Understanding the pathology of complex and heterogeneous central nervous system diseases such as multiple sclerosis (MS) has been greatly hampered by the dearth of histological specimens obtained serially during the disease. Clinicians are reluctant to perform invasive CNS biopsies on patients with white matter disorders, due to the potential injury to the patients.

The insight of CNS white matter neuropathology has been derived typically from occasional biopsies consisting of small tissue samples of unusual cases. Autopsy tissues have revealed important insights into CNS pathologies. However, autopsies usually derive from patients with end-stage disease and often have long postmortem delay artifacts due tissue degradation. It is therefore advantageous to have a noninvasive imaging tool to accurately quantify and better understand the chronic and non-fatal injury in CNS disease during the whole course of the individual patient.

Diffusion tensor imaging (DTI) is a commonly used MRI modality in CNS disease/injury diagnosis. However, the current use of DTI technique is not capable of resolving the complex underlying pathologies correctly, despite being considered better than other techniques.

BRIEF DESCRIPTION

In one aspect, a method is provided for determining diffusivity of multiple diffusion components within a tissue using diffusion magnetic resonance data representing a volume of the tissue. The method includes defining within the volume a plurality of candidate fibers having a direction. A possibility coefficient is calculated by a processor for each candidate fiber of the plurality of candidate fibers based on the magnetic resonance data and the direction of the candidate fiber. The possibility coefficient represents a likelihood that the candidate fiber exists in the volume. Candidate fibers associated with a possibility coefficient greater than a threshold value are selected by the processor to create one or more probable fibers. For each probable fiber of the one or more probable fibers, an axial diffusivity indicating a diffusion of water in the direction of the probable fiber and a radial diffusivity indicating a diffusion of water perpendicular to the direction of the probable fiber are calculated by the processor.

BRIEF DESCRIPTION OF THE DRAWINGS

FIGS. 3B and 3C are a flowchart of an exemplary method for determining diffusivities of fibers and isotropic components within a tissue.

FIG. 6 is an illustration of an exemplary optimization process of DBSI basis set.

DETAILED DESCRIPTION

Figure 1:
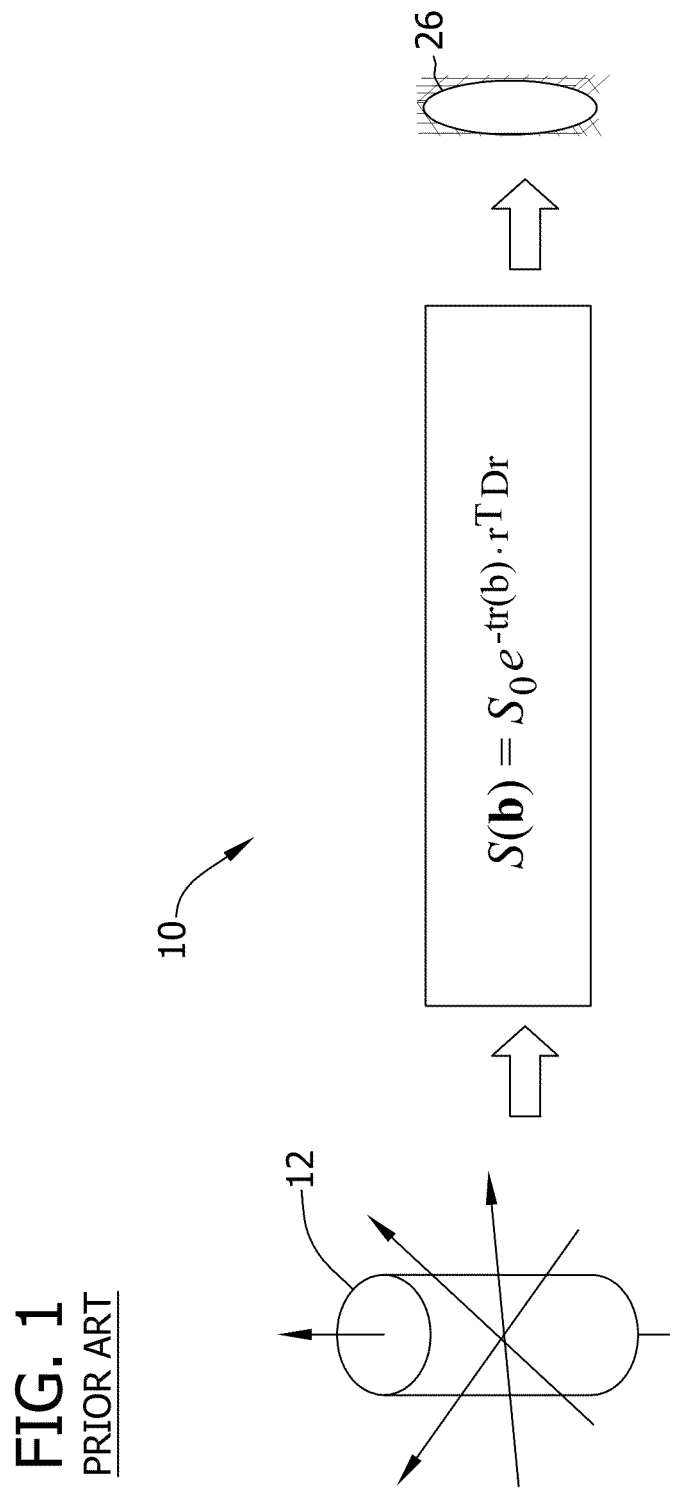
FIG. 1 is an illustration of diffusion magnetic resonance (MR) signal response when diffusion tensor imaging (DTI) is applied to a single white matter tract of coherent axonal fibers.

Embodiments provided herein employ a diffusion MRI technique to noninvasively study and quantify complicated CNS diseases in a noninvasive fashion without the limitation of invasive histological examinations.

Such embodiments facilitate improved results compared to diffusion tensor imaging (DTI). The directional diffusivities derived from DTI measurements describe water movement parallel to ($\lambda_\parallel$, axial diffusivity) and perpendicular to ($\lambda_\perp$, radial diffusivity) axonal tracts. We have previously proposed and validated that decreased $\lambda_\parallel$ is associated with axonal injury and dysfunction, and increased $\lambda_\perp$ is associated with myelin injury in mouse models of white matter injury.

The presence of inflammation, edema, or gliosis during CNS white matter injury may impact the DTI measurement. One significant effect of inflammation is the resulting isotropic component of diffusion, due to the increased extracellular water and the infiltrating immune cells. This component complicates the DTI measurements and distorts the estimated directional diffusivity and anisotropy preventing its accurate interpretation of underlying pathologies. In addition to inflammation, similar isotropic diffusion tensor component may result from the loss of CNS tissues in the chronic MS lesions, spinal cord injury (SCI), or traumatic brain injury (TBI). The currently used DTI protocol is not able to resolve this isotropic component or differentiate inflammation from tissue loss. Only an averaged diffusion tensor reflecting the overall effect can be obtained from existing DTI methods.

DTI fails to (1) correctly describe axonal fiber directions in crossing white matter tracts, or (2) accurately reflect the complex white matter pathologies such as vasogenic edema, inflammation, and tissue loss commonly coexisting with axonal and myelin damages. Even recently developed existing systems are not capable of resolving white matter pathologies in complex tissue scenarios.

A noninvasive process based on diffusion MRI technique is described herein to facilitate accurately quantifying the complex human CNS white matter pathology where the current DTI and its relevant improvements have failed. As an exemplary embodiment, diffusion basis spectrum imaging (DBSI) is implemented and provided herein to demonstrate the feasibility and detailed operation of the proposed novel process. The quantity and primary direction of diffusion tensor components within a tissue volume resulting from white matter pathology is determined using diffusion MRI before constructing the multi-tensor model. After the identification of each diffusion tensor component corresponding to individual pathology, the diffusivity and volume ratio of each component can be derived accordingly.

In some embodiments, the quantity of candidate fibers and their associated primary directions are calculated first by DBSI based on a combination of diffusion basis set best describing the measured diffusion magnetic resonance data. An isotropic diffusion component is also considered to improve the computation accuracy. Based on all candidate fibers' primary directions, DBSI is used to compute the axial diffusivity, indicating water diffusion parallel to the fiber, and radial diffusivity, indicating water diffusion perpendicular to the fiber. A diffusivity spectrum of isotropic diffusion components, such as those resulting from inflammation or tissue loss, as well as associated volume ratios of all candidate fibers and isotropic components may be calculated.

An exemplary embodiment employs diffusion basis spectrum imaging (DBSI) to facilitate an accurate diagnosis of CNS white matter pathology. Each diffusion tensor's directional diffusivity as well as its primary orientation is derived using the less stringent diffusion tensor acquisition schemes retaining DTI's applicability in clinical settings. Preliminary data in mouse corpus callosum, spinal cord injury, and phantoms demonstrates that DBSI is capable of identifying different underlying pathologies accurately estimating the extent of cell infiltration, axonal fiber density in corpus callosum of cuprizone treatment, as well as estimating tissue loss in chronic mouse spinal cord injury. Novel diffusion phantoms have also been designed and fabricated for a quantitative evaluation of DBSI and existing DTI methods.

The exemplary embodiment of diffusion MRI described herein resolves the multi-tensor complication resulting from diverse pathologies in CNS white matter to quantitatively derive diffusion parameters of crossing fibers as well as reflecting the actual pathologies. This unique capability of the proposed process and the exemplary DBSI method has the potential to differentiate acute inflammation from chronic tissue loss in patients. Such capability can estimate the extent of acute inflammation guiding the use of anti-inflammatory treatment and chronic tissue damage guiding the effort in axonal/neuronal preservation. There are many potential clinical applications of the proposed process. For example, it can document the efficacy of stem cell treatment in axonal regeneration by clearly estimating the isotropic component of the implanted cells while reflecting the axonal regeneration by quantifying the anisotropic component changes after cell transplantation. It could also be used to estimate the degree of CNS tumor growth by accurately estimating the isotropic tensor component representing the tumor cells. Methods described further facilitate evaluating the effectiveness of a drug in treating one or more medical conditions. For example, DBSI could be applied in clinical drug trial treating CNS diseases, tumors, and injury by accurately reflecting the progression of clinical and preclinical pathologies.

One important characteristic of DTI is its ability to measure diffusion anisotropy of CNS tissues for a detailed description of the underlying tissue injury based on the changed diffusion character. However, such measurement is not always obtainable in diseased tissues due to the complicated cellular responses to the pathology or the presence of crossing fibers.

The fundamental operation of DTI 10 can be explained by examining an MRI signal 12 under the influence of diffusion weighting gradients 14. When applying DTI to measure the single white matter tract of coherent axonal fibers, the MRI signal response can be expressed as shown in FIG. 1.

DTI assumes that there is only a pure coherent axonal fiber tract in the measured tissue and the signal response to diffusion weighting gradients is well described by the diffusion weighted (DW) profile. The insufficiency of DTI can be demonstrated by examining the diffusion ellipsoid responding to the different tissue components that typically seen in CNS tissues with and without pathology, as shown in FIG. 2.

Figure 2:
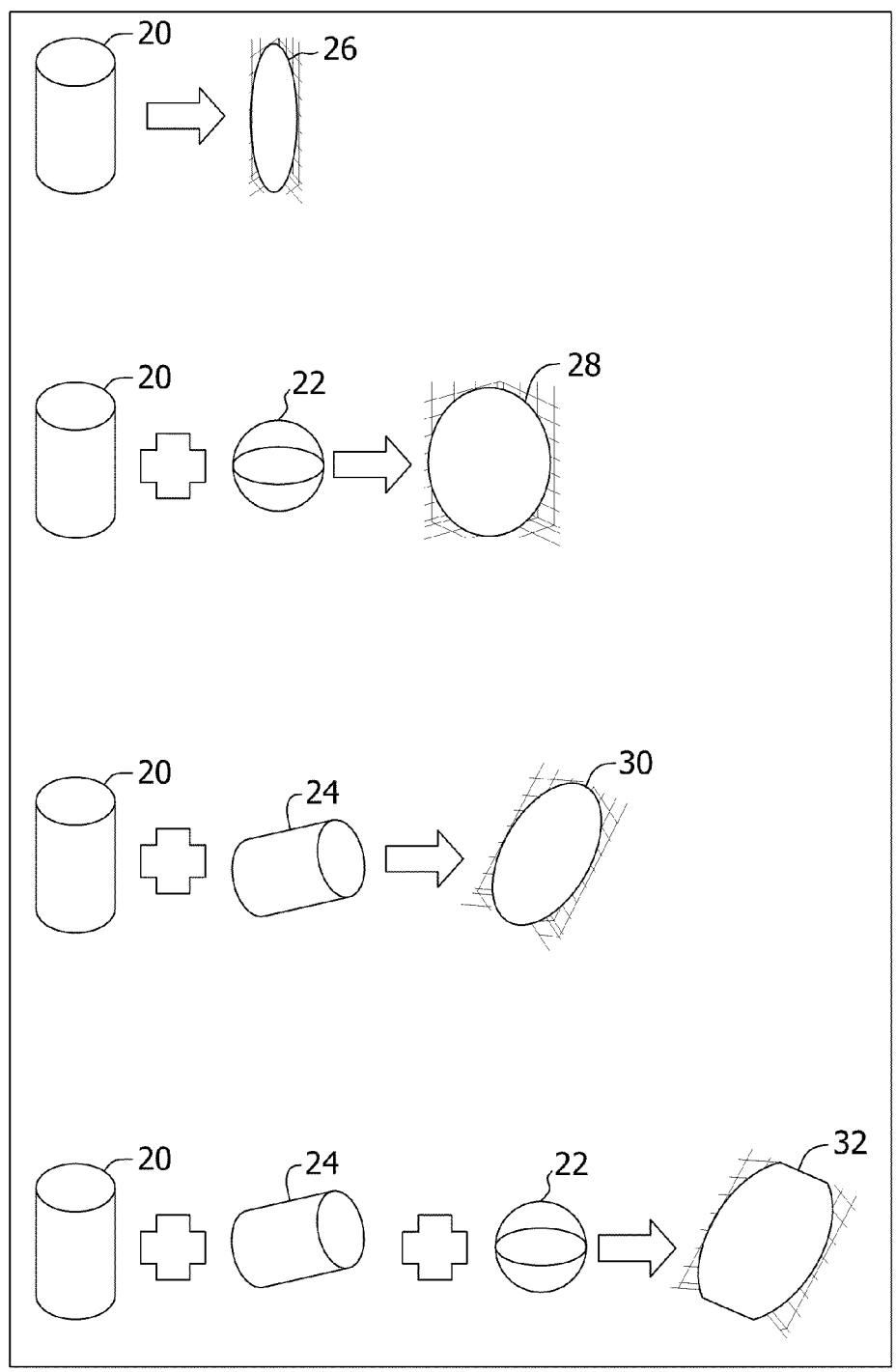
FIG. 2 is an illustration of exemplary DTI results corresponding to scenarios in which different tissue components are included within a scanned volume.

FIG. 2 illustrates exemplary DTI results corresponding to scenarios with the different tissue components (objects), including (A) ideal coherent single fiber 20 (spinal cord white matter or optic nerves), (B) fiber 20 plus an isotropic component 22 (tissue loss, inflammation, or edema), (C) two crossing fibers 24, and (D) two crossing fibers 24 with an isotropic component 22. If fiber 20 of (A) is of interest and the target for a DTI measurement as demonstrated, the correct DTI result for the ideal fiber result 26. Nevertheless, the various mixed conditions result in misrepresentations 28, 30, and 32 of the targeted fiber, which is the major shortcoming of DTI.

To definitively resolve the issue regarding the utility of directional diffusivity in detecting white matter injury in MS and/or other CNS white matter disorders, a careful evaluation was performed on the mouse model of cuprizone intoxication that is widely employed to examine the mechanisms of CNS white matter de- and re-myelination. It has been demonstrated that axonal injury, inflammation, and demyelination co-exist at 4 weeks of continuous cuprizone feeding. Our previous DTI studies showed that decreased $\lambda_{\parallel}$ correlated with histology-confirmed axonal injury, while no significant increase of $\lambda_{\perp}$ was seen, thus failing to reflect the concurrent demyelination. A Monte Carlo simulation modeling the three underlying pathologies was performed. Preliminary results suggested that the presence of infiltrating inflammatory cells exerted significant effect on the derived directional diffusivity reducing both $\lambda_{\parallel}$ and $\lambda_{\perp}$, exaggerating the effect of axonal injury while diminishing the sensitivity to demyelination. This finding suggests that the current DTI analysis is suboptimal to accurately depict the underlying pathology in diseases with inflammation, such as MS.

Figure 3A:
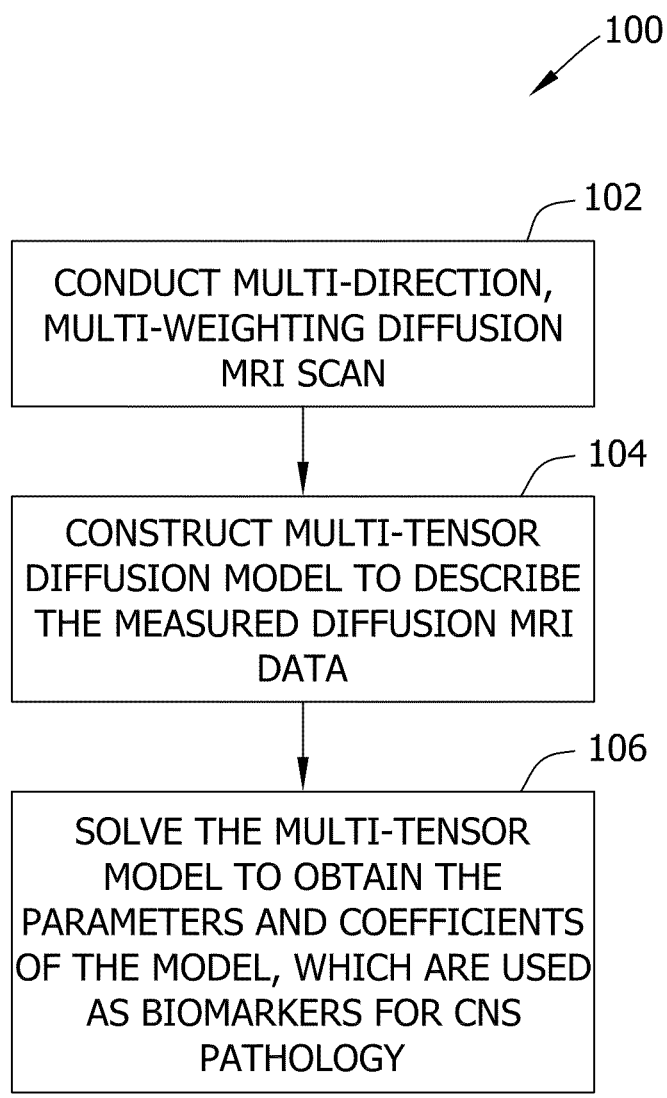
FIG. 3A is a flowchart of an exemplary noninvasive process to quantify complex CNS white matter pathology.

To address this shortcoming of DTI, a novel process allowing an accurate description of the underlying tissue pathology is described herein. FIG. 3A is a flow chart 100 illustrating the basic steps required to detect and differentiate the underlying CNS white matter pathologies. First, a multi-direction, multi-weighting diffusion MRI scan is conducted 102 utilizing a signal acquisition and processing component. A multi-tensor diffusion model is constructed 104, and the multi-tensor model is solved 106 to obtain the parameters and coefficients of the model.

Figure 3C:
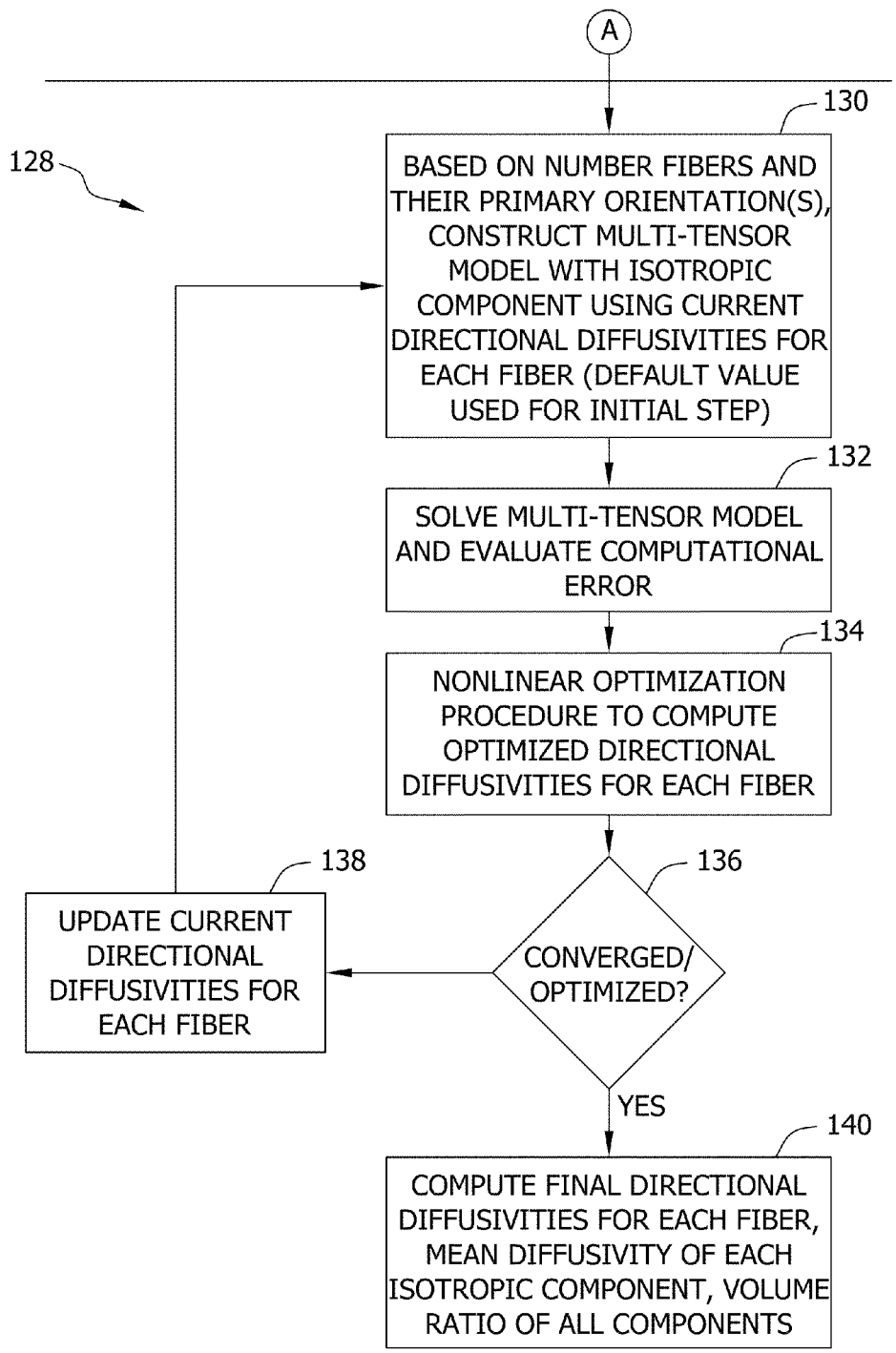

In the exemplary embodiment, a multiple-tensor based DBSI, or diffusivity component, is provided (FIGS. 3B and 3C). The method illustrated may be used to determine diffusivity of each diffusion tensor component within a tissue. In the multiple-tensor based DBSI, an MRI scan is performed 108. In performing the MRI scan, subjects are set up 110 in MRI scanner and a multi-direction diffusion MRI scan is performed 112. From the performed 112 MRI scan, a diffusion MRI dataset is obtained 114.

After an MRI scan is performed 108, number of fibers and their primary orientation is determined 115. In determining 115 the number of fibers and their primary orientation a diffusion MRI signal is projected 116 onto diffusion a basis and a computation error is evaluated. Next, a nonlinear optimization procedure is performed 118 to compute optimized directional diffusivities for diffusion basis. It is determined 120 whether the fibers are converged and optimized.

If the fibers are determined 120 not to have been converged and optimized, the current directional diffusivities for both diffusion basis and isotropic components are updated 122. After update 122, a diffusion basis using current directional diffusivities and isotropic component is constructed 124 and projected 116 is performed again. If the fibers are determined 120 to have been converged and optimized, the number of fibers based on projection of diffusion MRI data onto optimized diffusion basis set is determined 126.

After the number of fibers and their primary orientation is determined 115, diffusivities of each fiber and isotropic components are determined 128. In determining 128 the diffusivities of each fiber and isotropic components, a multi-tensor model with isotropic component using current directional diffusivities for each fiber is constructed 130. A multi-tensor model is solved 132 and evaluated for computational error. Next, a nonlinear optimization procedure is performed 134 to compute optimized directional diffusivities for each fiber. It is determined 136 whether the fibers are converged and optimized. If the fibers are determined 136 not to have been converged and optimized, the current directional diffusivities for each fiber are updated 138 and the multi-tensor model is constructed 130 again. If the fibers are determined 136 to have been converged and optimized, a final directional diffusivity for each fiber is computed 140. Additionally, a mean diffusivity of each isotropic component, and a volume ratio of all components is computed 140.

Figure 4A:
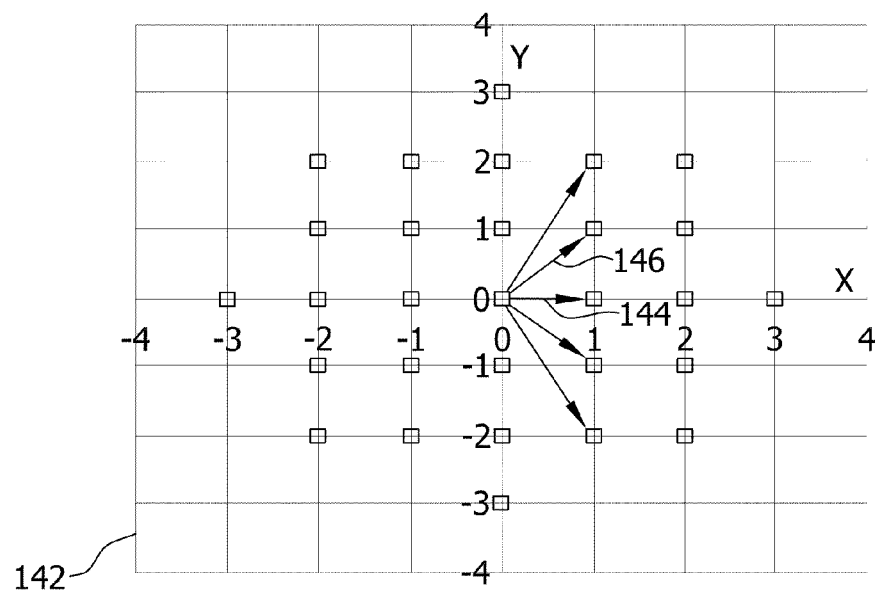
FIG. 4 is an illustration of the design of an exemplary 99-direction diffusion-weighting scheme.
Figure 4B:
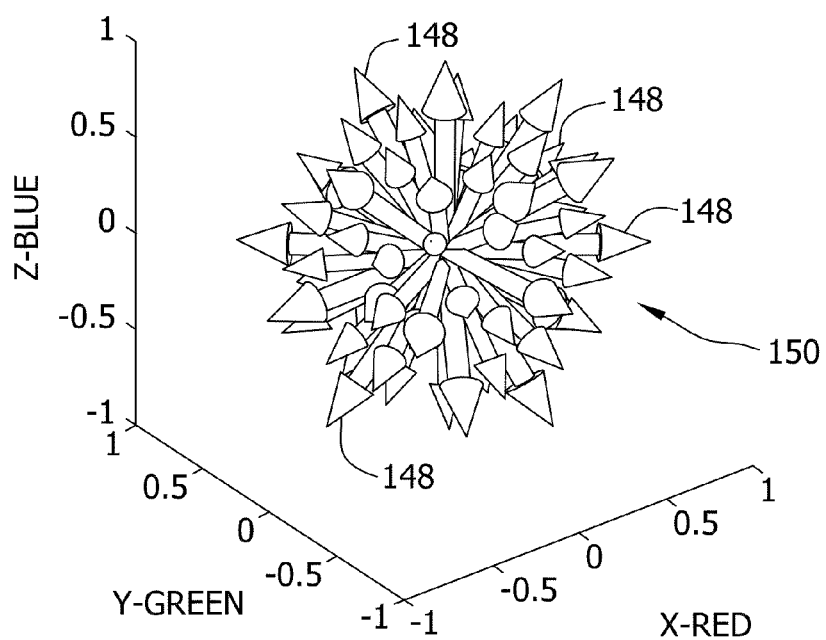

FIG. 4 is an illustration of the design of an exemplary 99-direction diffusion-weighting scheme. As shown in the 2D schematic 142, each diffusion-weighting direction is selected based on the grid point location. For example, the first diffusion weighting direction 144 is from origin (0, 0) to grid point (1, 0), the second diffusion weighting direction 146 is from (0, 0) to (1, 1), and so on. In the exemplary embodiment, 99 diffusion directions are selected based on the 3D grid locations 148 shown by 3D model 150.

An advantage of designing the 99-direction diffusion weighting gradients 148 based on regular grid locations is that the directions are uniformly sampled in the 3D space. No matter which direction the real axonal fiber orients, the scheme has no bias to it. Another advantage is that the weighting of diffusion gradients is naturally set as different values in this grid-based design, which is favorable in terms of determining multiple isotropic diffusion components.

However, embodiments described herein are not limited to this particular design. Any diffusion-weighting scheme that samples the whole 3D space uniformly and provides multiple weighting factors will work well resolving multiple-tensor reflecting the CNS white matter pathology as proposed.

Similar to diffusion basis function decomposition (DBFD) proposed by Ramirez-Manzanares et al., DBSI employs the following multi-tensor model as the first-step analysis:

$$S_k = \sum_{i=1}^{N} S_i \exp(-\vec{b}_k \cdot \lambda_\perp) \exp(-\vec{b}_k \cdot (\lambda_\parallel - \lambda_\perp) * \cos^2(\theta_i)), \quad \text{(Equation 1)}$$

$$k = 1, 2, \ldots, 99$$

In Equation 1, $\vec{b}_k$ is $k^{th}$ diffusion gradient (k=1, 2, ..., 99); $\lambda_\parallel$ is the axial diffusivity and $\lambda_\perp$ is the radial diffusivity; $S_k$ is the measured diffusion weighted signal at direction $\vec{b}_k$; $\theta_i$ is the angle between the diffusion gradient $\vec{b}_k$ and the primary direction of $i^{th}$ diffusion basis; N is the number of diffusion basis components uniformly distributed in 3D space.

Figure 5:
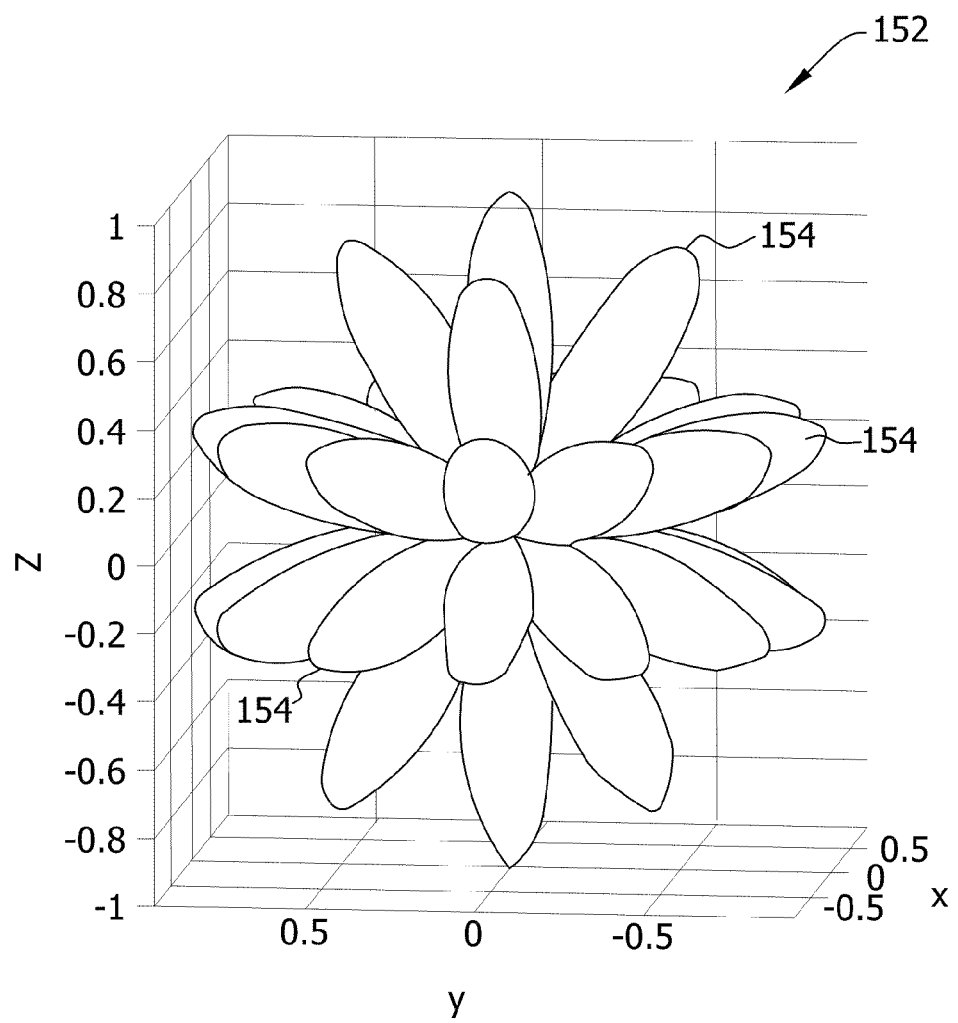
FIG. 5 is an illustration of an exemplary diffusion basis set for DBSI.

FIG. 5 illustrates a diffusion basis set 152 with 40 diffusion bases 154. As shown in FIG. 5, each diffusion basis 154 represents a candidate fiber orientation, and the diffusion basis 154 set is uniformly distributed in the 3D space. As described by Equation 1, the real fiber is treated as the linear combination of the entire diffusion basis set.

Instead of presetting $\lambda_\parallel$ and $\lambda_\perp$ at fixed values for the entire diffusion basis in DBFD, DBSI performs a nonlinear searching to estimate the optimal values of $\lambda_\parallel$ and $\lambda_\perp$ best fitting the acquired diffusion weighted data. Isotropic tensor component is uniquely incorporated in DBSI to improve the accuracy, as shown in Equation 2.

$$f(\lambda_\parallel, \lambda_\perp, d) = \quad \text{(Equation 2)}$$

$$\min \left\| \sum_{k=1}^{99} \left\{ S_k - \sum_{i=1}^{N} S_i \exp(-\vec{b}_k \cdot \lambda_\perp) \exp(-\vec{b}_k \cdot (\lambda_\parallel - \lambda_\perp) \cos^2(\theta_i)) - S_{N+1} \cdot \exp(\vec{b}_k \cdot d) \right\}^2 \right\|$$

In Equation 2, $S_i$(i=1, 2, ..., N+1)≥0, $\lambda_\parallel$ and $\lambda_\perp$ are directional diffusivities, and d is the diffusivity of isotropic diffusion component with d, $\lambda_\parallel$, and $\lambda_\perp$ selected as the optimization variables. Unknown coefficients $S_i$(i=1, 2, ..., N+1) are not optimization variables because are not independent to $\lambda_\parallel$ or $\lambda_\perp$. $S_i$ is computed using the least square estimation under the nonnegative constraint ($S_i$≥0) and the basic principle of sparsity as employed in DBFD during the nonlinear optimization procedure. After the optimization, the number of fibers and their primary axis directions are estimated similar to DBFD.

A unique feature of this disclosure is that the shape of each diffusion basis is not prefixed as in DBFD method. Instead, the basis shape is optimized during the optimization process to estimate both $\lambda_\parallel$ and $\lambda_\perp$. This optimization process is demonstrated in FIG. 6 using a single axonal fiber 156 as the example. In the exemplary embodiment, experimental data is fitted by the linear combination of a diffusion basis set 154 with fitting error improved through iterations 158, 160, 162, and 164 until the optimal coefficients of linear combination of diffusion basis are estimated 166. In the exemplar embodiment, iteration 158 has a fitting error of 0.6, iteration 160 has a fitting error of 0.4, iteration 162 has a fitting error of 0.2, and iteration 164 has a fitting error of 0.04. Isotropic component is also considered according to Equation 2 in this process (not shown) to improve the optimization accuracy.

Figure 7A:
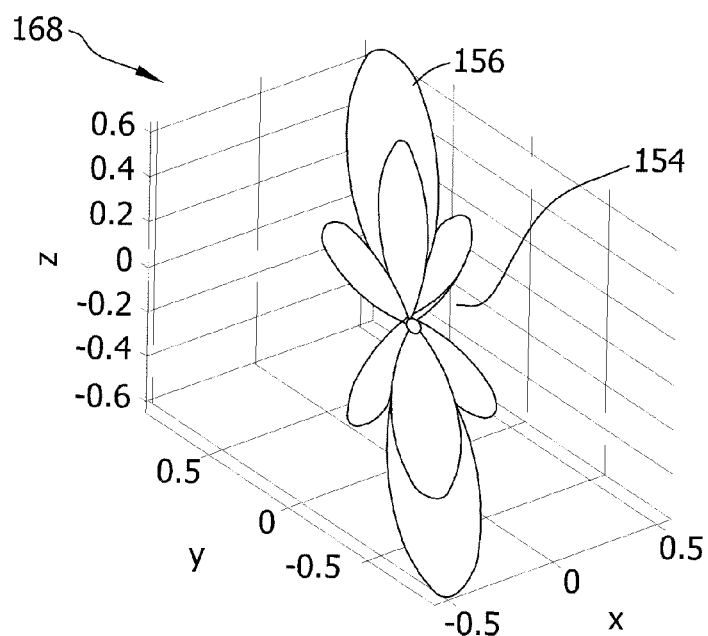
FIG. 7 is an illustration of determining the number of fibers and primary directions of candidate fibers using DBSI.
Figure 7B:
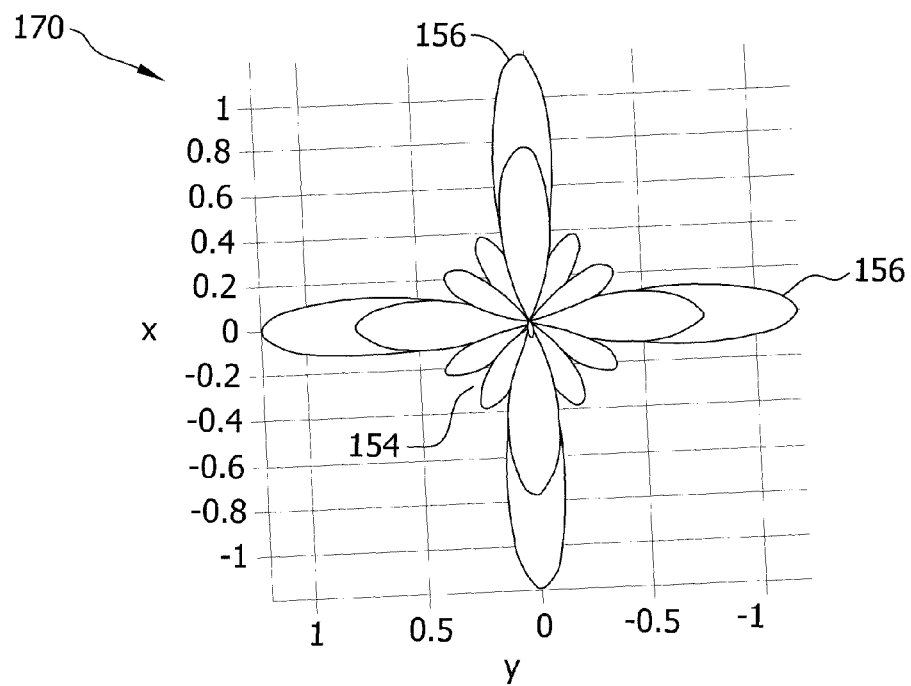

As shown in FIG. 7, the diffusion basis 154 with direction close to that of the axonal fiber 156 contributes more significantly to the linear combination with higher magnitude of the coefficients $S_i$. The diffusion basis 154 with direction away from that of the axonal fiber 156 has limited contribution to the coefficient of linear combination of the basis set fitting the experimental data. Both single 168 and two-fiber 170 tracts are demonstrated.

DBSI determines the number and primary direction of fibers according to the description of Equation 1. Each coefficient is associated with one diffusion tensor basis at a particular direction. These preliminary coefficients are grouped based on the magnitude and the closeness in orientations of the associated basis diffusion tensor. Coefficients smaller than a threshold determined by raw signal SNR are ignored. Significant coefficients with closely oriented (within 15 degrees) diffusion basis tensors are grouped as one fiber. The threshold of 15 degrees is set based on the desired angular resolution. Once the grouping process is complete, the averaged direction of the grouped diffusion basis is defined as the primary direction of the fiber.

Based on the number of fiber (anisotropic tensor) components and associated primary directions, DBSI constructs another multi-tensor model with the assumption of axial symmetry. A set of isotropic tensor components are included in the model:

$$S_k = \sum_{i=1}^{L} S_i \exp(-\vec{b}_k \cdot \lambda_{\perp\_i}) \exp(-\vec{b}_k \cdot (\lambda_{\parallel\_i} - \lambda_{\perp\_i}) \cos^2(\phi_i)) + \sum_{j=1}^{M} S_{L+j} \cdot \exp(\vec{b}_k \cdot d_j) \right\}^2 \quad \text{(Equation 3)}$$

In Equation 3, $S_k$ is the measured diffusion weighted signal at diffusion gradient direction $\vec{b}_k$. L is the number of estimated fibers in the imaging voxel. $\lambda_{\parallel\_i}$ and $\lambda_{\perp\_i}$ (i=1, 2, . . . , L) are the axial and radial diffusivity of the ith fiber. $\phi_i$ is the angle between the diffusion gradient $\vec{b}_k$ and the primary direction of ith estimated fiber. $d_j$(j=1, . . . , M) are the diffusivities of M isotropic diffusion components. $S_i$(i=1, 2, . . . , L) are fiber volume ratios and $S_i$(i=L+1, L+2, . . . , L+M) are the volume ratio of isotropic components.

Based on this multi-tensor model, a nonlinear optimization search is constructed as following:

$$h(\lambda_{\parallel\_i}, \lambda_{\perp\_i}, i = 1 \ldots L) = \quad \text{(Equation 4)}$$

$$\min \left\| \sum_{k=1}^{99} \left\{ S_k - \sum_{i=1}^{L} S_i \exp(-\vec{b}_k \cdot \lambda_{\perp\_i}) \exp(-\vec{b}_k \cdot (\lambda_{\parallel\_i} - \lambda_{\perp\_i}) \cos^2(\phi_i)) - \sum_{j=1}^{M} S_{L+j} \cdot \exp(\vec{b}_k \cdot d_j) \right\}^2 \right\|$$

Equation 4 is subject to $S_i$(i=1, 2, . . . , L+M)≥0. In this optimization procedure, isotropic diffusivity $d_j$(j=1, . . . , M) are not selected as optimization variables to reduce the total number of the free variables. Instead, isotropic diffusivities are uniformly preset within the physiological range. Directional diffusivities, $\lambda_{\parallel\_i}$ and $\lambda_{\perp\_i}$(i=1, . . . , L) of each anisotropic component are the only free variables to be optimized based on the experimental data and Equation 4 with the nonnegative constraint ($S_i$≥0) under least square sense. Finite signal energy is incorporated to effectively prevent the nonnegative least square from over-fitting the noisy data while retaining the numerical accuracy of the solution. All diffusion tensor's volume ratios $S_i$(i=1, 2, . . . , L+M) based on T2-weighted (i.e., non-diffusion weighted) image intensity are computed with least square fitting during the nonlinear optimization procedure.

Figure 8:
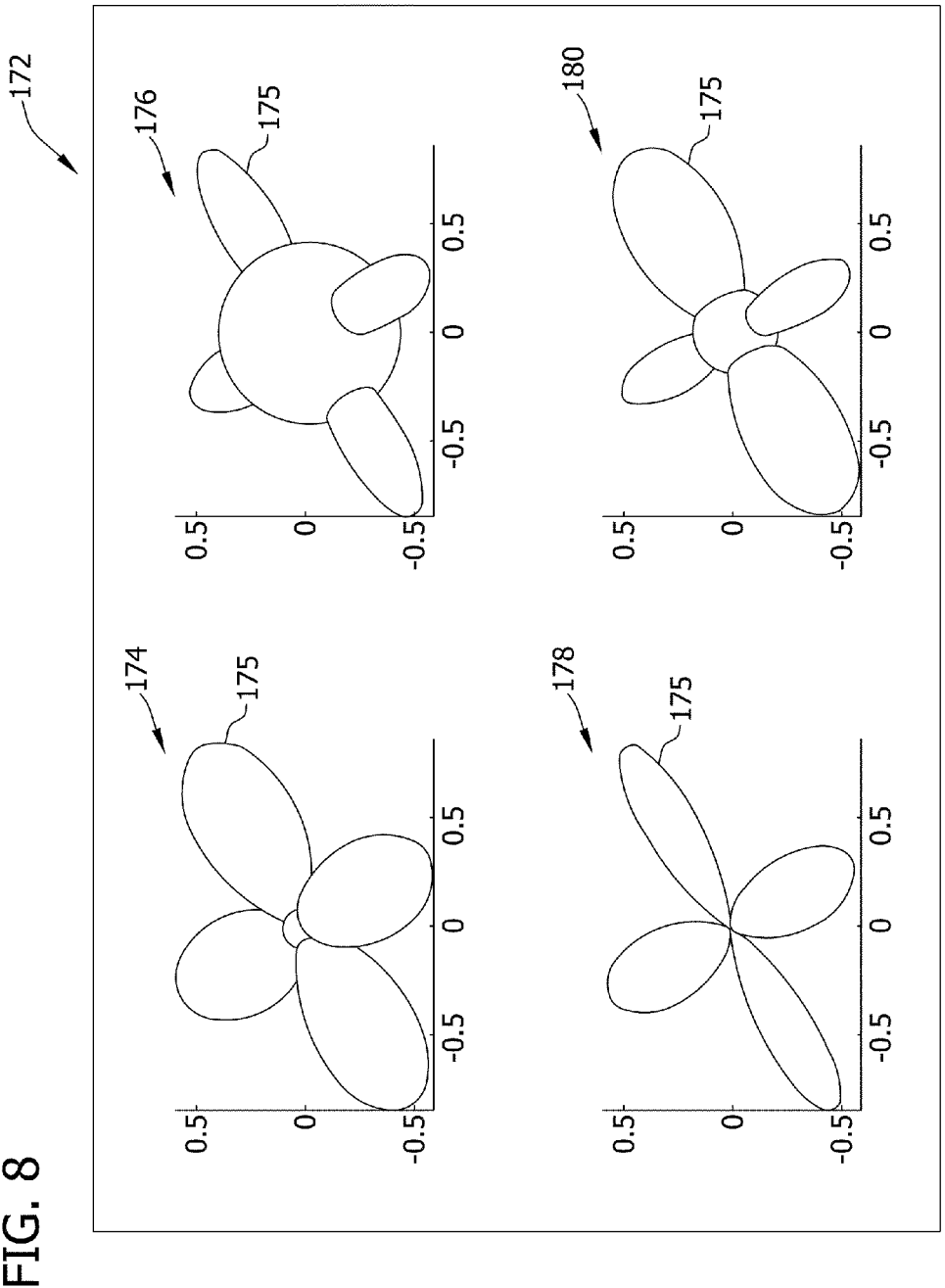
FIG. 8 is an illustration of an exemplar optimization process for determining the directional diffusivity of each candidate fiber, isotropic components and corresponding volume ratios using DBSI.

In one embodiment, an optimization process 170, as shown in FIG. 8, is used to search the best directional diffusivities for each candidate fiber and compute all the volume ratios of each diffusion component. Process 170 demonstrates two crossing fibers (L=2). In such an embodiment, a first optimization 174 includes candidate fibers 175 with a fitting error of 0.4. Likewise, a second optimization 176 includes candidate fibers 175 with a fitting error of 0.2, a third optimization 178 includes candidate fibers 175 with a fitting error of 0.1, and a fourth optimization 180 includes candidate fibers 175 with a fitting error of 0.02

After the fourth optimization 180, the fitting error is smaller than 2%, which falls within the acceptable range. Therefore, the directional diffusivity of each candidate fiber 175, and corresponding volume ratios computed after the optimization 180 are determined as the final DBSI results. In the DBSI algorithm, the nonlinear optimization procedure is executed based on criteria including maximal iteration numbers, tolerance of mesh size, tolerance of variable, tolerance of function, accepted accuracy, and many other criteria set according to the need. Once some or all of these criteria are met according to the preset level, the optimization procedure is considered satisfactorily fit the data and the optimization stops.

Figure 13:
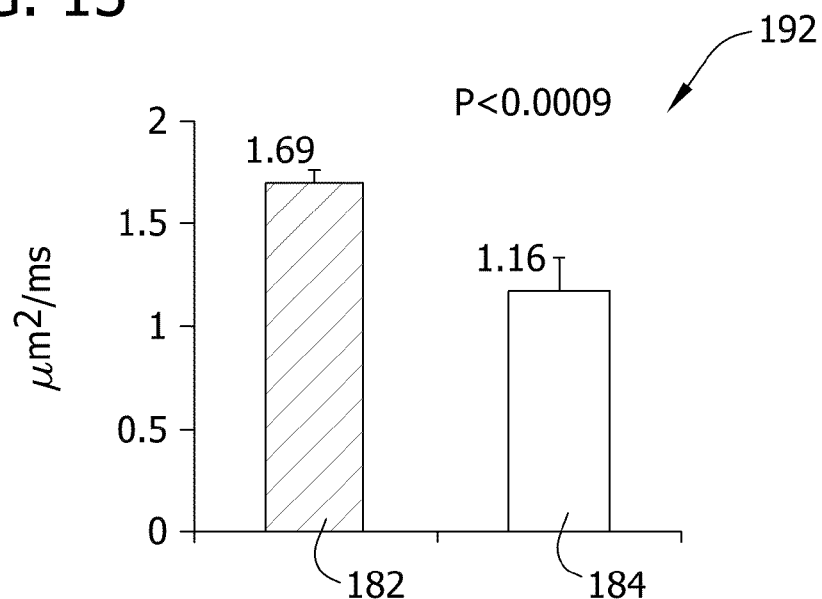
FIG. 13 is a graph of the axial diffusivity of the DBSI of FIG. 12.
Figure 16:
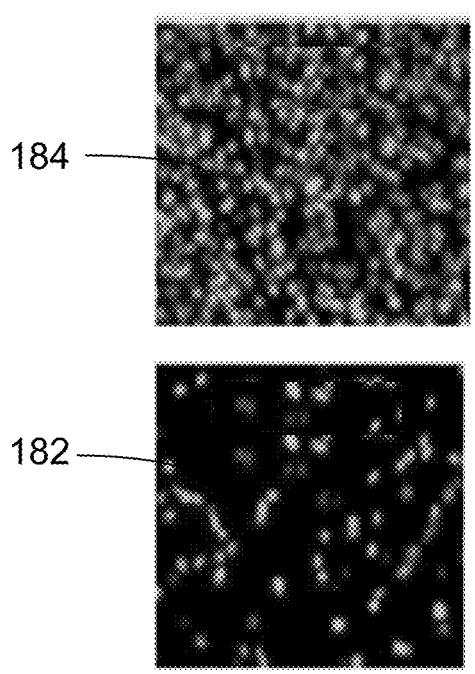
FIG. 16 is an illustration of DAPI staining results quantifying inflammation in the presence of axonal injury and demyelination.

To determine the capability of the newly developed DBSI approach in detecting and differentiating the underlying co-existing pathology, the cuprizone model was again employed to compare conventional DTI with the new DBSI analysis. Striking contrast between DTI and DBSI was observed at the corpus callosum from C57BL/6 mice treated with cuprizone for 4 weeks. DTI failed to detect demyelination and overestimated axonal injury even with 99-direction diffusion weighting, while offering no information on inflammation. However, DBSI correctly reflected the presence of demyelination (FIG. 9—MBP), axonal injury (FIG. 10—DTI; FIG. 13—DBSI, FIG. 14—SMI-31), and inflammation (FIGS. 16 and 17).

Figure 9:
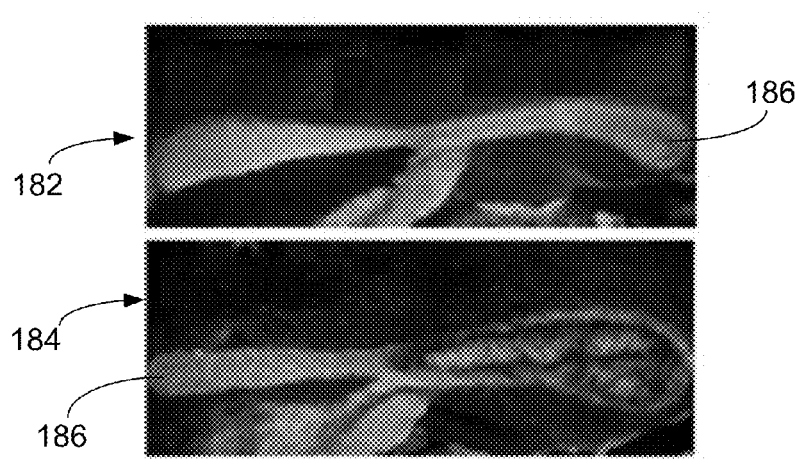
FIG. 9 is an illustration of myelin basic protein of mouse corpus callosum after 4 weeks of cuprizone treatment.
Figure 11:
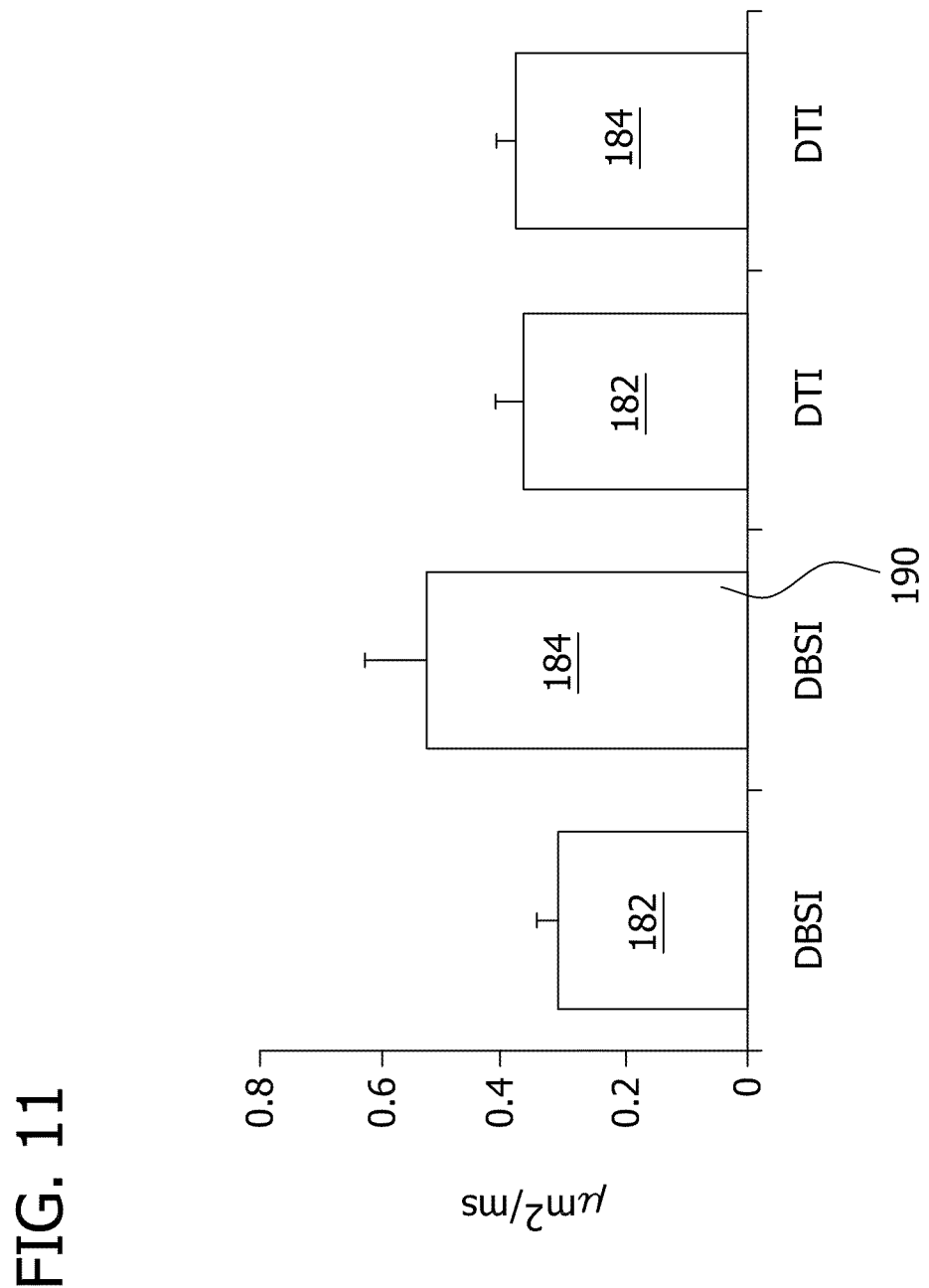
FIG. 11 is a graph of the radial diffusivity derived using DBSI and DTI of FIG. 9.
Figure 12:
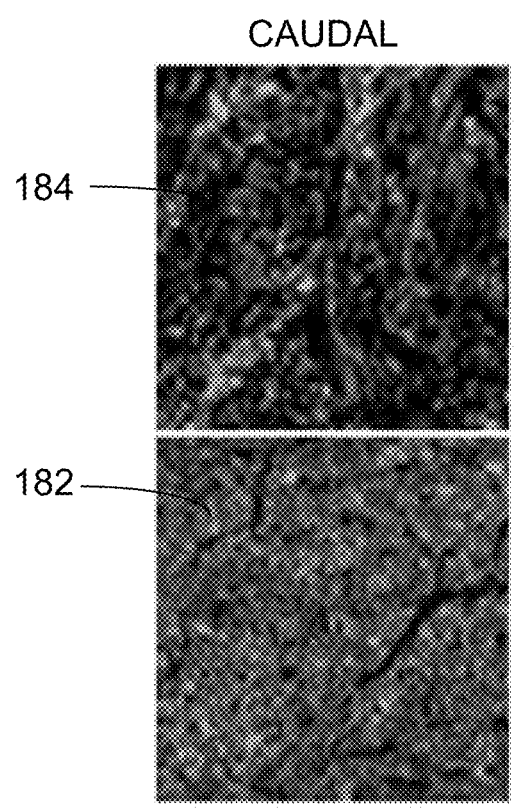
FIG. 12 is an expanded region of myelin basic protein staining in the caudal region of FIG. 9.

FIG. 9 is an illustration of Sagital view of corpus callosum from a control 182 and a 4-week cuprizone fed male C57BL/6 mice (n=5) 184 examined using DTI and DBSI (FIG. 11). As shown by myelin basic protein 186 immunostaining, significant demyelination in the caudal corpus callosum is seen by reduced MBP-positive area 186 (FIG. 9) and increased radial diffusivity 190 (FIG. 11) derived using DBSI. Consistent with previous reports, lack of increase in DTI derived radial diffusivity failed to reflect the histological finding of demyelination 184 (FIG. 11).

Figure 10:
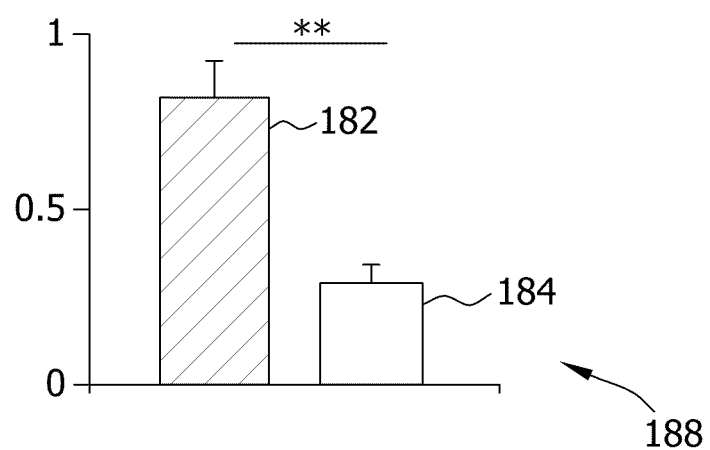
FIG. 10 is a graph of DTI-derived axial diffusivity reflecting axonal injury in the region of demyelinating area of FIG. 9.
Figure 14:
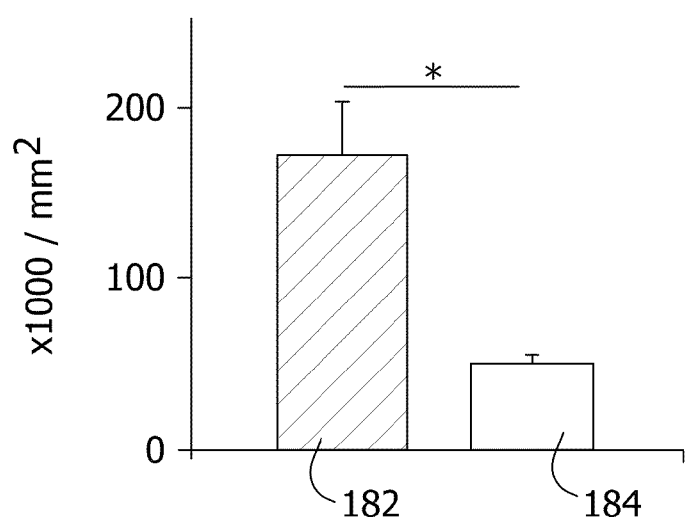
FIG. 14 is a graph of the SMI-31 stain of the region examined by DBSI of FIG. 12.
Figure 15:
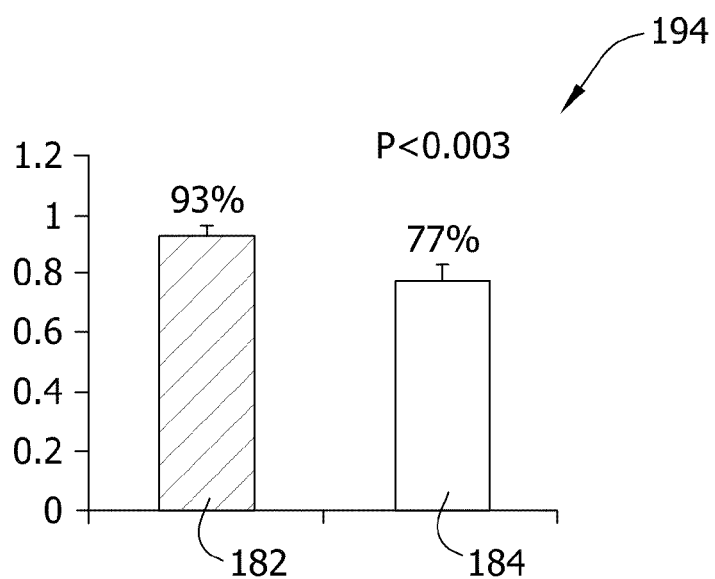
FIG. 15 is a graph of axonal fiber tract density was also derived using DBSI expressing as volume ratio of the DBSI of FIG. 12.

FIG. 10 illustrates that similar to previous findings that decreased DTI derived axial diffusivity was seen in corpus callosum from 4-week treated mice 184 (n=5, −43%) from control 182, DBSI derived axial diffusivity 192 (FIG. 13) decreased (−31% from the control 182) to reflect the histology proved axonal injury (FIG. 14). The axonal fiber tract density 194 (FIG. 15) was also derived using DBSI expressing as volume ratio. Due to the infiltrating inflammatory cells, the density of axonal fiber tracts was reduced from 93% to 77%, a finding not available for conventional DTI.

Figure 17:
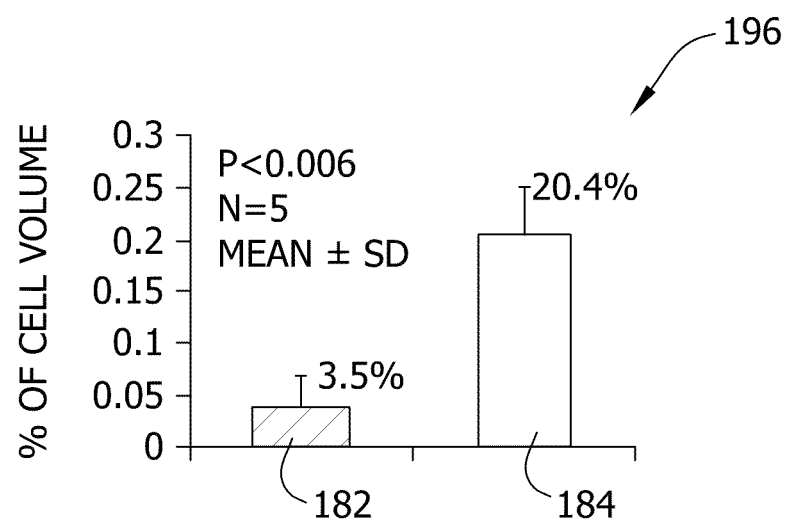
FIG. 17 is a graph of the percentage of inflammatory cell infiltration thought to be in the cells of the illustration of FIG. 16.

FIG. 17 illustrates inflammatory cell infiltration 196 derived using DBSI. In such an embodiment, the inflammatory cell infiltration 196 is to be 16.9% (20.4-3.5) of total volume in 4-week cuprizone treated corpus callosum 184, above the baseline 3.5% cellular content. This is consistent with the significantly increased DAPI positive stains in the same region (FIG. 16), information has not been available using DTI.

Figure 18:
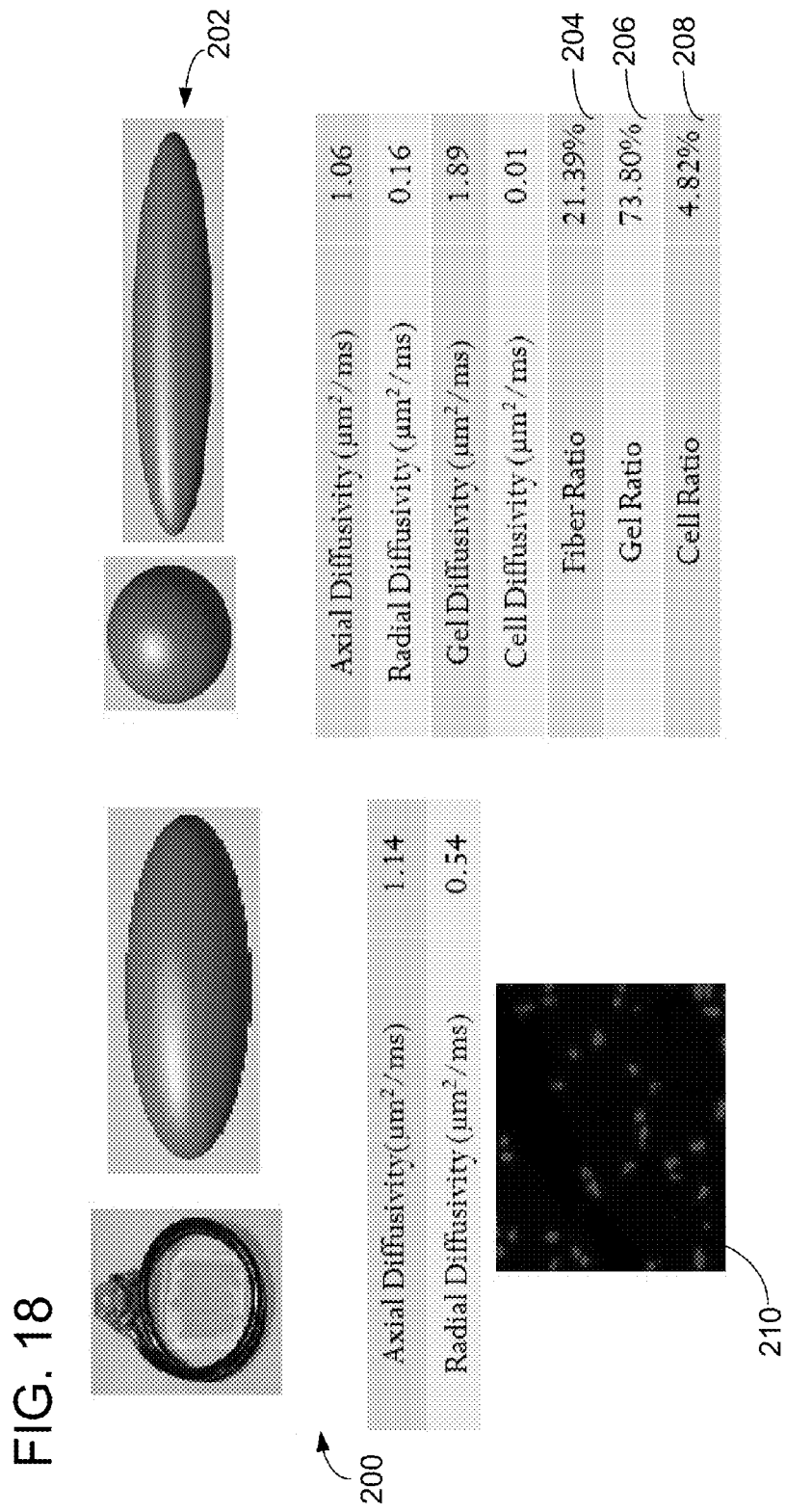
FIG. 18 is an exemplary phantom of mouse trigeminal nerves embedded in gel with known in vivo DTI character.

In another embodiment, 99-direction diffusion weighted images are analyzed following one or more operations described above to determine the number of intravoxel fibers and isotropic components on a laboratory fabricated phantom containing mouse trigeminal nerves with known in vivo DTI character and isotropic gel as shown in FIG. 18.

Diffusion weighted MRI was performed on the phantom using 99 distinct diffusion weighting gradients for both DTI 200 and DBSI 202 analysis. For the pure gel, DTI 200 and DBSI 202 estimated the isotropic apparent diffusion coefficient to be identical at 1.91 μm²/ms suggesting both methods are accurate for simple medium. When examining the mixture of fiber/gel in this phantom using DTI 202, the isotropic gel component was not identified. In addition, the true fiber diffusion anisotropy (FA=0.82±0.005) determined previously using an in vivo high resolution DTI was not obtained. In contrast, using the newly proposed DBSI identified a fiber ratio 204 of 21%, a gel ratio 206 of 74%, and a cell ratio of 5% with correct fiber diffusion anisotropy of FA=0.83. The anisotropy was compared because it was previously observed that diffusion anisotropy is preserved in vivo and ex vivo in mouse nerve fibers.

Another fiber phantom 210 was built to contain two mouse trigeminal nerves crossing each other at 90° with isotropic gel. As expected that DTI failed to identify the two crossing fibers or the gel. In contrast, DBSI was able to identify the presence of two fibers crossing at 90° estimating fiber orientations of (1, 0, 0) and (0, 0, 1). The diffusion anisotropy of the two fibers was estimated to be 0.81 and 0.83 respectively. Correct volume ratio was also estimated by DBSI to report 19% of (1, 0, 0) fiber, 19% of (0, 0, 1) fiber, 52% of gel, and 10% of cell component.

In the chronic CNS injury, tissue loss is common. Current DTI techniques have not been able to correctly reflect the status of chronic tissue injury. In a mouse spinal cord injury model, we examined the non-injured and moderately injured cord tissues. In the non-injured white matter of the mouse spinal cord, the DTI derived diffusion parameters were ADC=0.29 μm²/ms, axial diffusivity=0.69 μm²/ms, radial diffusivity=0.12 μm²/ms, and FA=0.85. These are comparable with those obtained using DBSI where ADC=0.29 μm²/ms, axial diffusivity=0.69 μm²/ms, radial diffusivity=0.10 μm²/ms, and FA=0.85. Both DTI and DBSI were successful in describing the non-injured white matter characteristics. However, when the moderately injured spinal cord tissues were examined, the DTI failed to capture the underlying pathology, i.e., the extent of tissue loss, resulting in overestimating axial diffusivities thus underestimating the severity of the injury. In contrast, DBSI was able to estimate that there is a 10% tissue loss in the injured white matter.

Methods described herein facilitate determination of an axial diffusivity, a radial diffusivity, and/or a volume ratio of a scanned volume of tissue with increased accuracy relative to known methods, which are distinguishable at least as follows.

Figure 19:
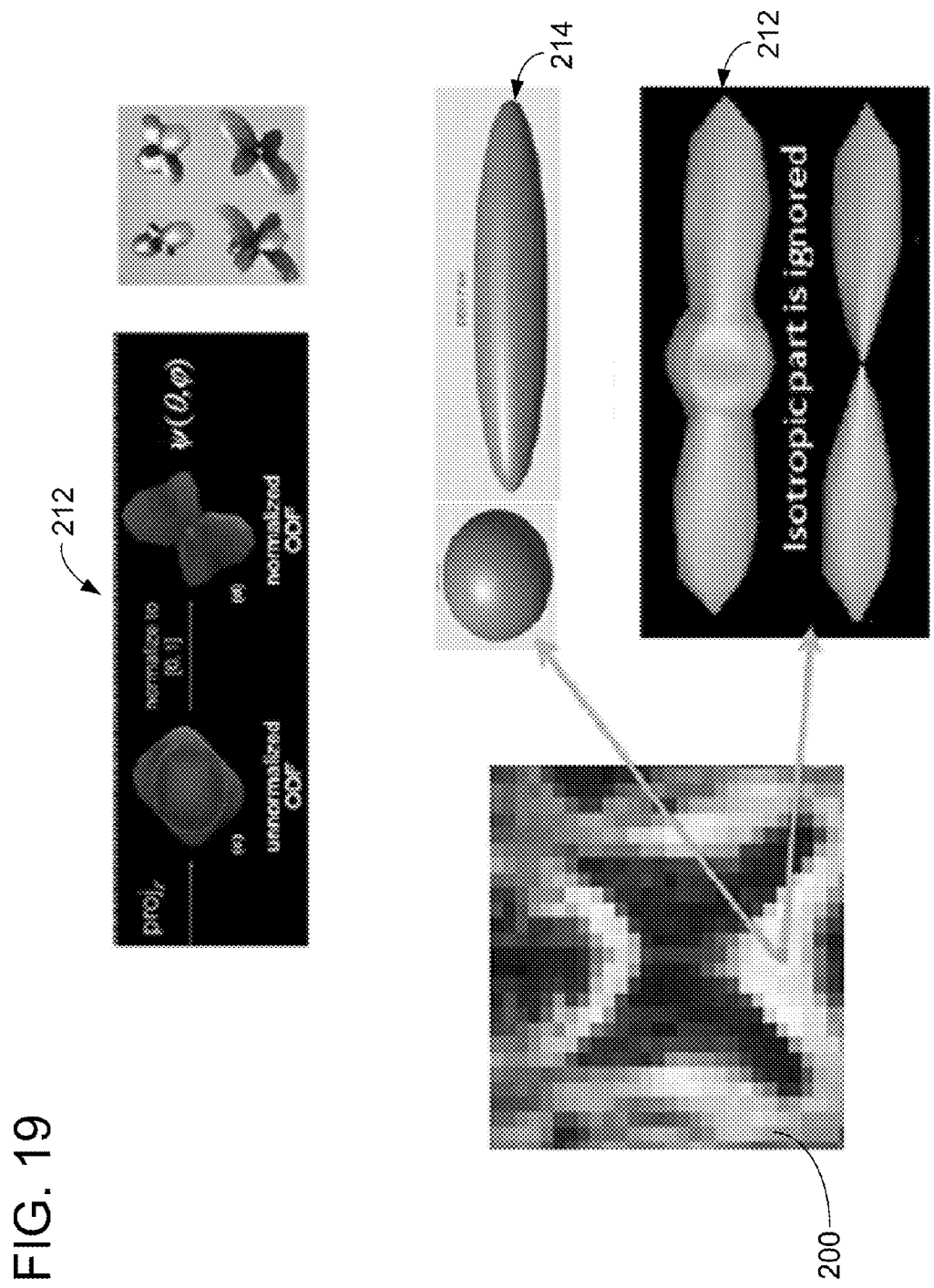
FIG. 19 is a comparison of diffusion spectrum imaging (DSI) and DBSI from a human subject.

FIG. 19 is a comparison of diffusion spectrum imaging (DSI) 212 and DBSI 214 from human subjects 216. DSI 212 is a method that attempts to directly measure the probability distribution function of the displacement of water molecules without an assumption of tissue structure or the shape of probability distribution function. It was proposed to identify multiple fibers within an image voxel. The use of orientation distribution function (ODF) by DSI effectively estimates angles of crossing fibers. However, its ODF based analysis does not offer other crucial quantitative information of water diffusion relevant to tissue physiology and pathology such as the apparent diffusion coefficients, diffusion anisotropy, or the volume ratio of different components. Therefore, DSI's applications are limited to fiber tracking.

The presence of an isotropic component within the image voxel is an important biomarker for cell infiltration, edema, and tissue loss. As shown in FIG. 19, the isotropic diffusion component is ignored in DSI 212 operation for the better estimation of the fiber orientation. In contrast, DBSI 214 quantitatively separates the isotropic from fiber component with accurate isotropic diffusivity assessment.

Operationally, DSI requires high diffusion weighting gradients of various magnitudes and directions to accurately estimate the ODF, a typically impractical challenge on regular clinical MR scanners. In contrast, DBSI facilitates operation with the clinically used diffusion weighting gradient strength and smaller number of directions. Thus, DBSI may be performed on clinical MR scanners with typical hardware resources.

Figure 20:
FIG. 20 is a diffusion tensor imaging (DTI) for mouse trigeminal nerve embedded in gel.
Figure 21:
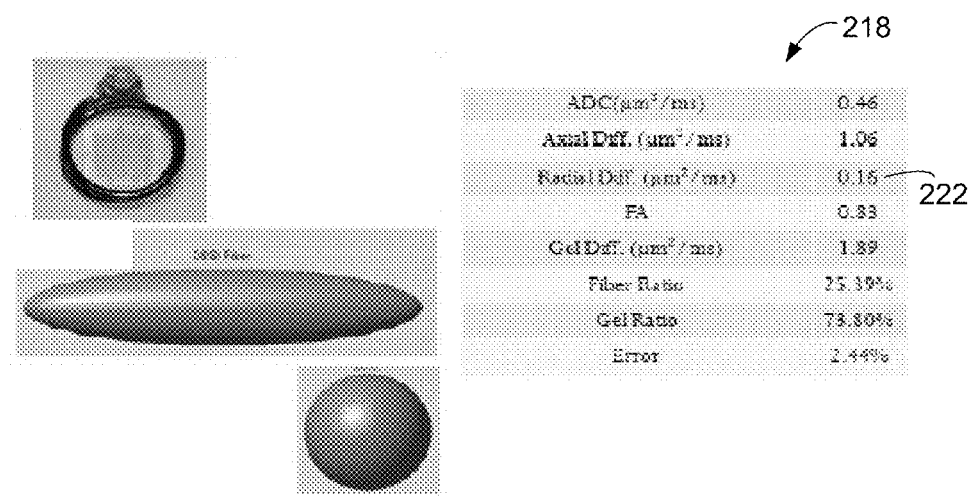
FIG. 21 is a DBSI for mouse trigeminal nerve embedded in gel.

FIG. 20 is a diffusion tensor imaging (DTI) 216 for mouse trigeminal nerve embedded in gel, and FIG. 21 is a DBSI 218 for mouse trigeminal nerve embedded in gel. DTI 216 derived radial diffusivity is very dependent on the tissue environment, and inaccurate assessment is common due to both the intra- and inter-voxel partial volume effect as demonstrated in FIG. 20. Using a simple yet realistic phantom constructed from fixed mouse trigeminal nerves and gel, as described above and as shown in FIG. 21, DTI 216 significantly over estimated the radial diffusivity 220, while DBSI 218 correctly quantified diffusivities 222, anisotropy, and volume ratios of all components.

This phantom study demonstrates the superior results enabled by DBSI in quantifying the overwhelming isotropic component within the image voxel and reporting correct diffusion properties of both the fiber and its environment. Embodiments described herein facilitate correctly estimating the extent of axonal loss noninvasively (e.g., in a clinical setting).

Figure 31:
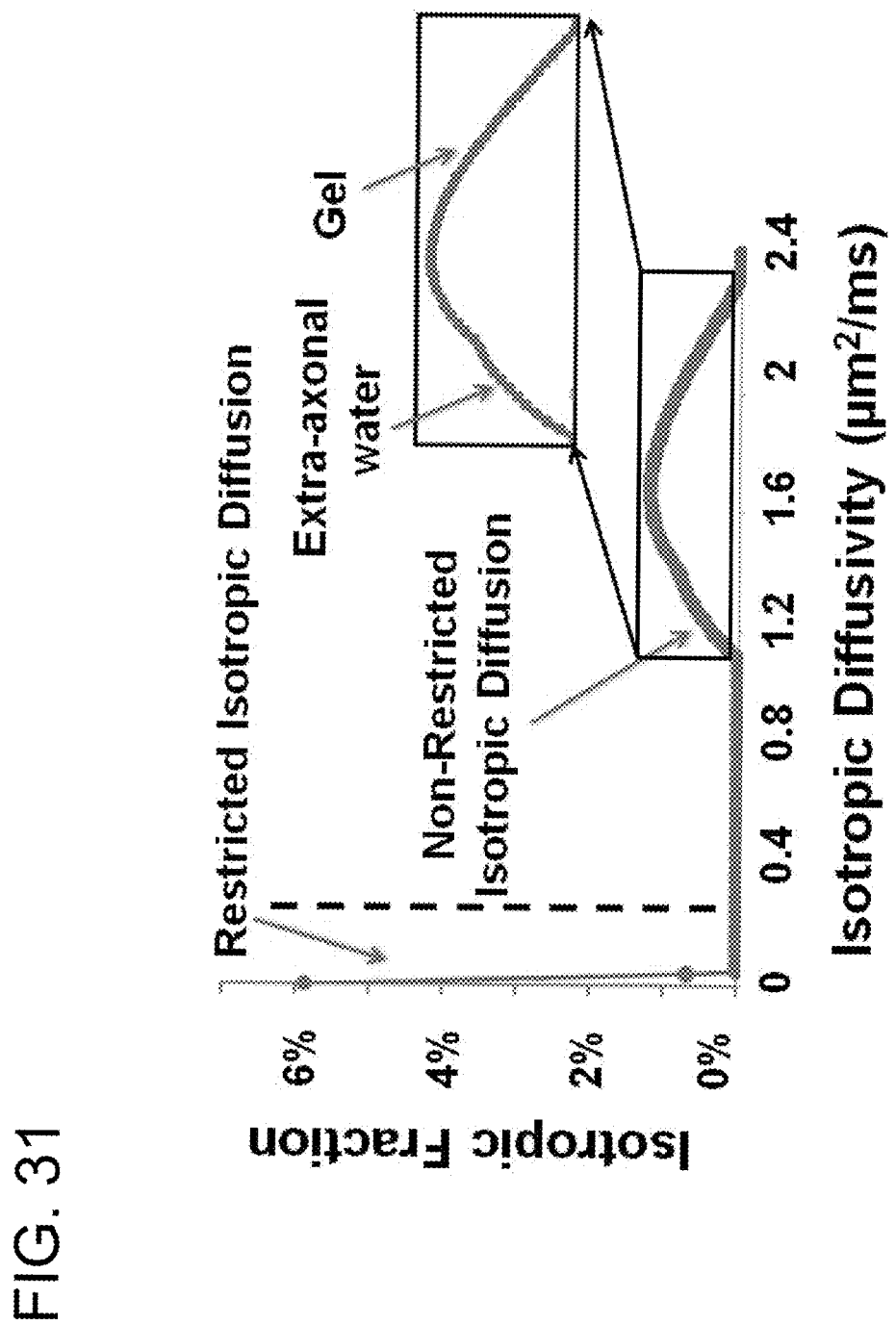
FIG. 31 is an illustration of a typical DBSI-derived spectrum of isotropic diffusivity from a fixed mouse trigeminal nerve juxtaposed with gel.

In one embodiment, eight trigeminal nerves from 4 normal male C57BL/6 mice were isolated after fixation. Diffusion MR spectroscopy was performed at 19° C. using a custom-built surface coil with the following parameters (common to all nerve fiber measurements): max b=3200 (s/mm2), repetition time (TR) 2 s, echo time (TE) 49 ms, time between application of gradient pulses (Δ) 20 ms, duration of diffusion gradient on time (δ) 8 ms, number of averages 4, 99-direction diffusion weighting gradients 44. Three diffusion tensor components were observed: anisotropic diffusion (75.9±2.6%: axon fibers), restricted isotropic diffusion (12.1±0.99%: cells), and non-restricted isotropic diffusion (12.1±2.5%: extra-axonal and extracellular water). The assignment of cell and water components was based on the DBSI-derived spectrum of isotropic diffusion (FIG. 31).

Figure 28A:
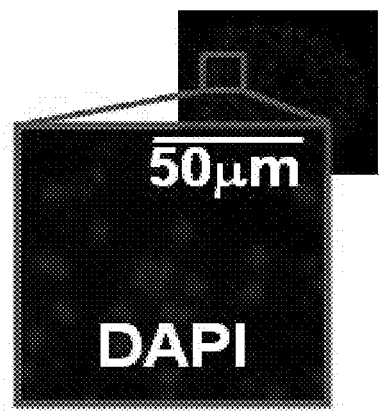
FIG. 28 is an illustration of a DAPI and SMI-31 staining of a fixed mouse trigeminal nerve and a comparison of isotropic diffusion spectra with gel.
Figure 28B:
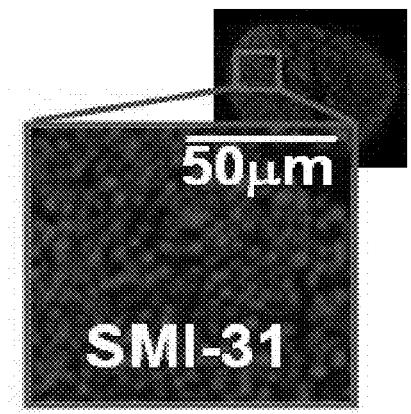
Figure 29:
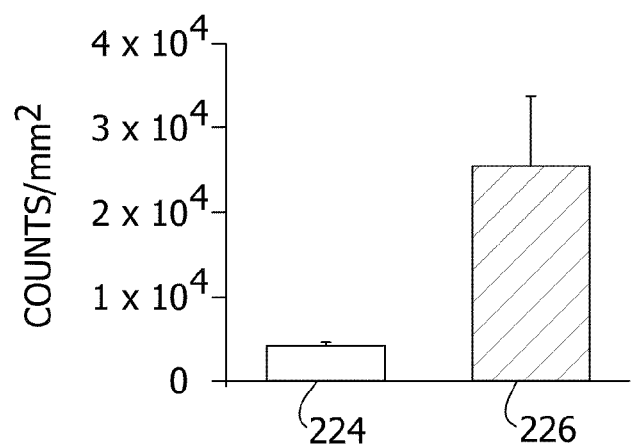
FIG. 29 is a graph of the nucleus and axon counts by IHC of FIG. 29.
Figure 30:
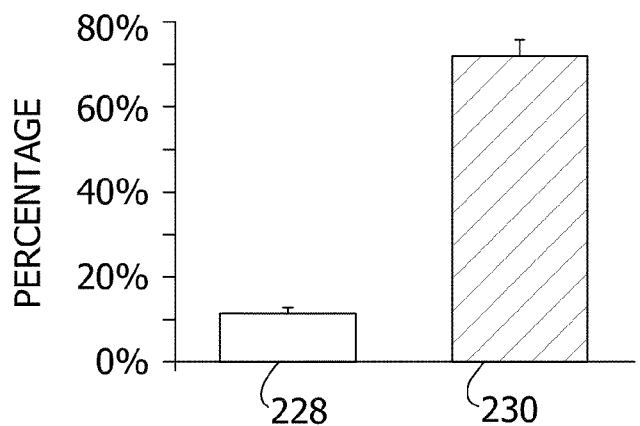
FIG. 30 is a graph of the DBSI derived cell percentage and fiber percentage of FIG. 29.

FIG. 28A, 28B illustrates a DAPI 224 and SMI-31 226 staining of a fixed mouse trigeminal nerve and a comparison of isotropic diffusion spectra with gel examined at. In such an embodiment, nucleus and axon staining was performed using 4',6'-diamidino-2-phenylindole (DAPI) and phosphorylated neurofilament (SMI-31) to count cells (4109±629/mm2) and axons (25434±8505/mm2) (FIG. 29). The powder-average effect of the 25% (FIG. 30) isotropic diffusion component in the fixed trigeminal nerve is apparent when comparing $\lambda_\parallel$ and $\lambda_\perp$ derived using DBSI ($\lambda_\parallel$=1.07±0.05 μm2/ms; $\lambda_\perp$=0.12±0.01 μm2/ms) vs. DTI ($\lambda_\parallel$=0.77±0.03 μm2/ms; $\lambda_\perp$=0.17±0.02 μm2/ms). Compared to DBSI, DTI underestimated $\lambda_\parallel$ by 28%, while overestimating $\lambda_\perp$ by 42%. Five fiber-gel samples were examined at 19° C. using DBSI to quantify anisotropic and isotropic diffusion, and T2W MRI to quantify total gel signal intensity.

Figure 32:
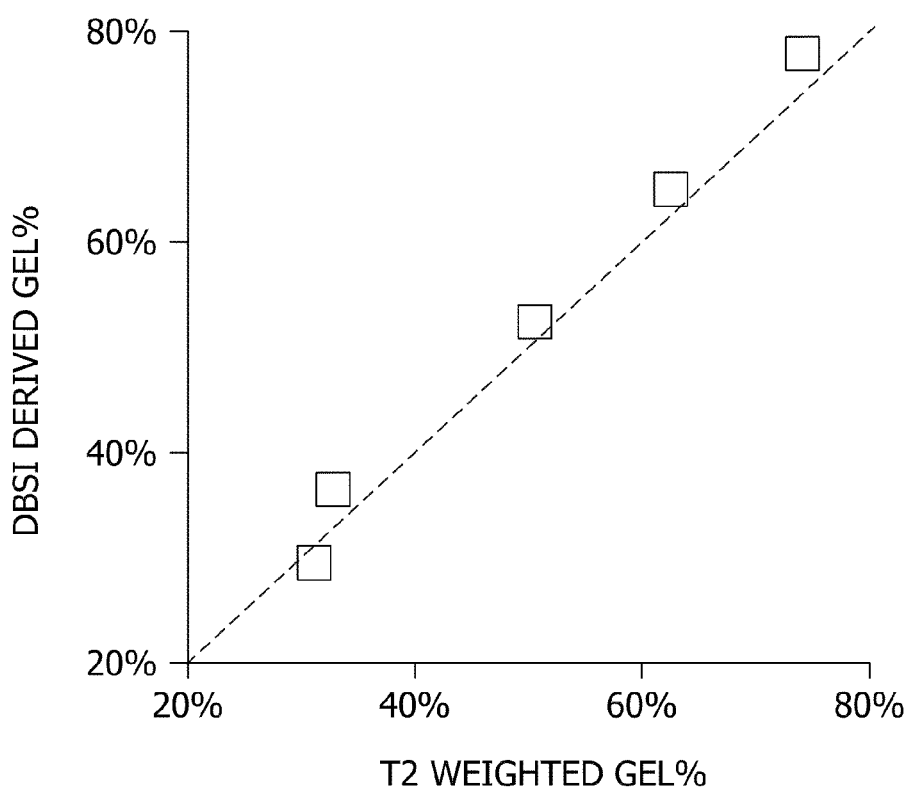
FIG. 32 is a comparison of DBSI-derived gel fractions to those measured by T2W MRI signal intensity.
Figure 33:
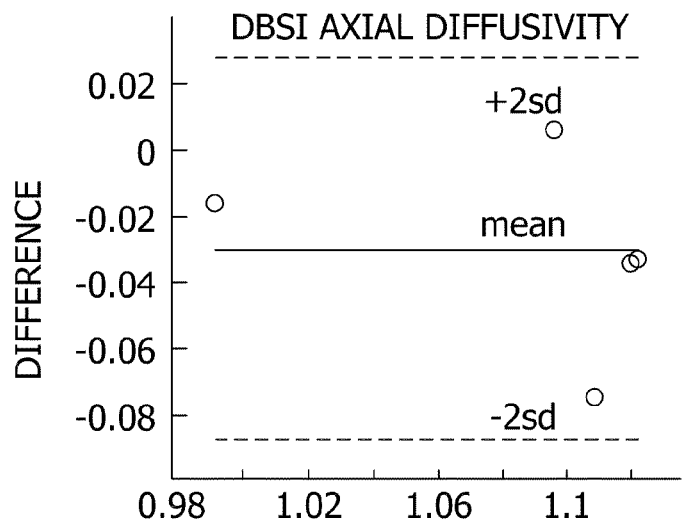
FIG. 33 is a graph of $\lambda_\parallel$ derived from trigeminal nerves with and without gel.
Figure 34:
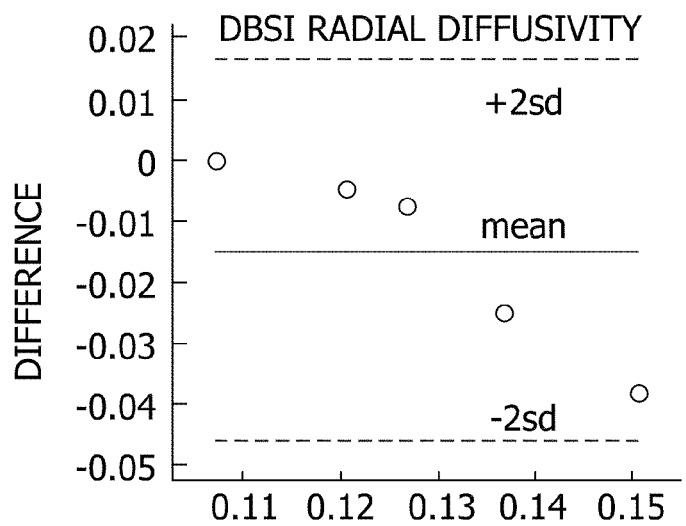
FIG. 34 is a graph of $\lambda_\perp$ derived from trigeminal nerves with and without gel.

The DBSI-determined gel water fraction closely matches that determined using T2W MRI as shown in FIG. 32, suggesting the potential of DBSI to estimate edematous water from more freely diffusing water in regions of tissue loss. The derived fiber directional diffusivities with and without gel are comparable as shown in FIGS. 33 and 34, indicating that DBSI can correctly assess fiber diffusion properties in the presence of edema or tissue loss.

Figure 35:
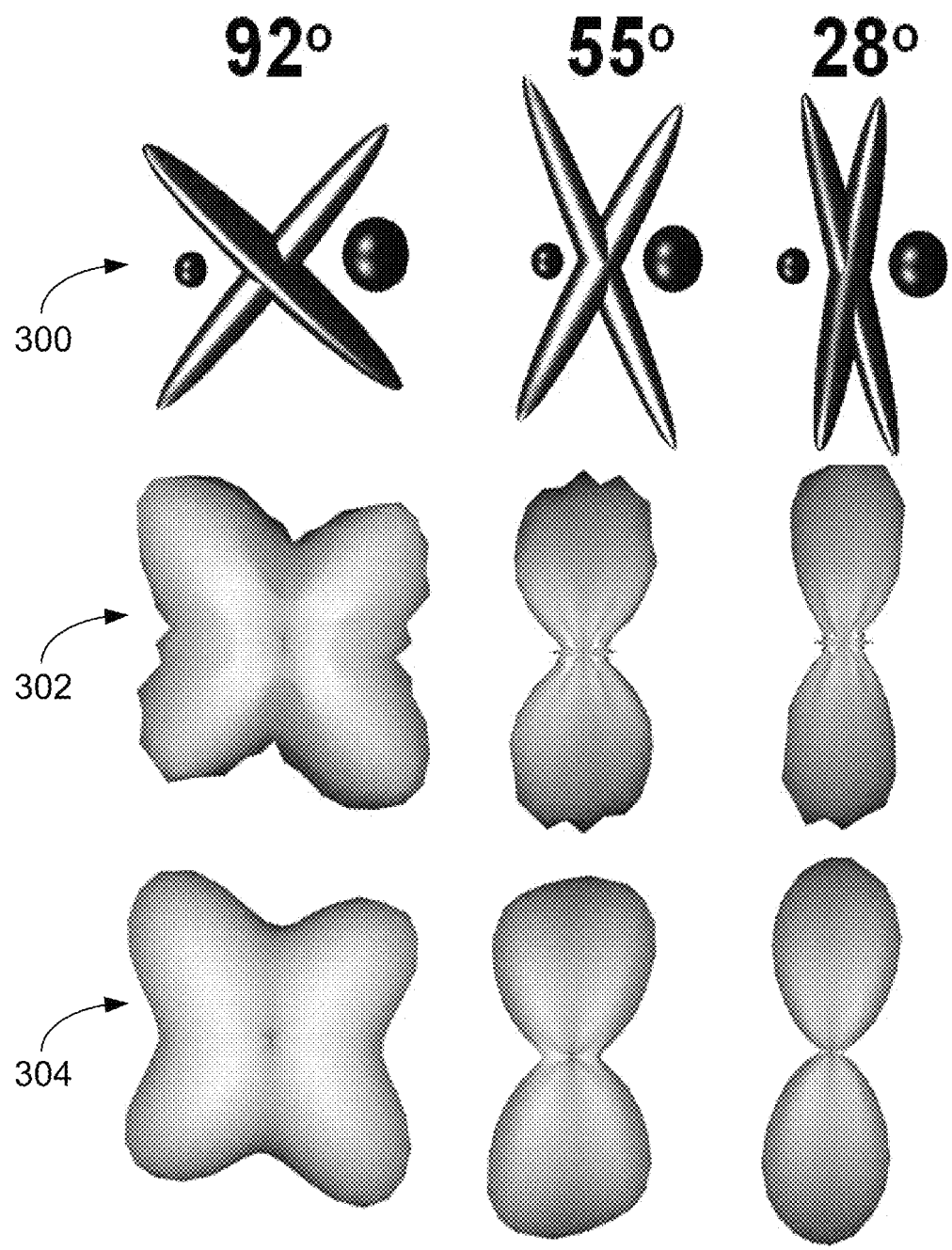
FIG. 35 is an illustration of six fixed trigeminal nerves grouped into three pairs of crossing fibers at 32°, 58°, and 91° juxtaposed with 2% agarose gel.

FIG. 35 is an illustration of six fixed trigeminal nerves grouped into three pairs of crossing fibers at 32°, 58°, and 91° juxtaposed with 2% agarose gel. DBSI-estimated crossing fiber angles 300 compare favorably with those derived using an orientation distribution function (ODF) by DSI 302 and general q-sampling imaging (GQI) 304. DBSI-quantified mean fiber 300$\lambda\|$=1.14±0.06 μm2/ms, $\lambda^\perp$=0.12±0.02 μm2/ms agreed well with measured values for a single fiber without gel $\lambda\|$=1.07±0.05 μm2/ms, $\lambda^\perp$=0.14±0.02 μm2/ms. For 91°, 58°, 32° phantoms, DBSI-derived gel percentages were 15%, 14%, and 50%, in close agreement with T2W MRI determined 18%, 13%, and 45%. DSI 302 and GQI 304 failed to resolve crossing FIGS. 33 and 34 comparable $\lambda\|$ (A), $\lambda^\perp$ (B) derived from trigeminal nerves with and without gel was confirmed by Bland-Altman plots.

Figure 36:
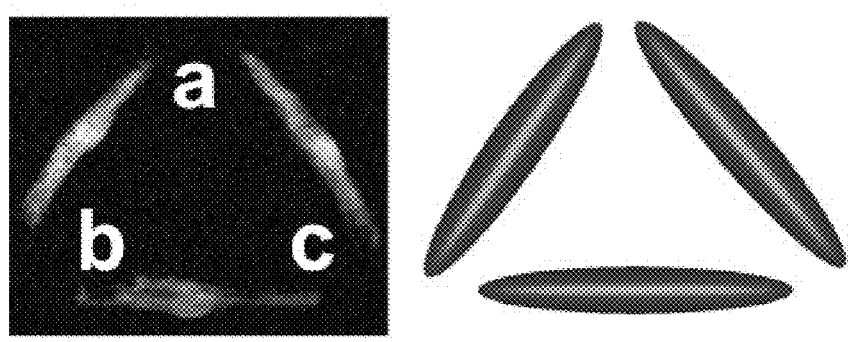
FIG. 36 is an illustration of a three-fiber crossing phantom forming a triangle.
Figure 37A:
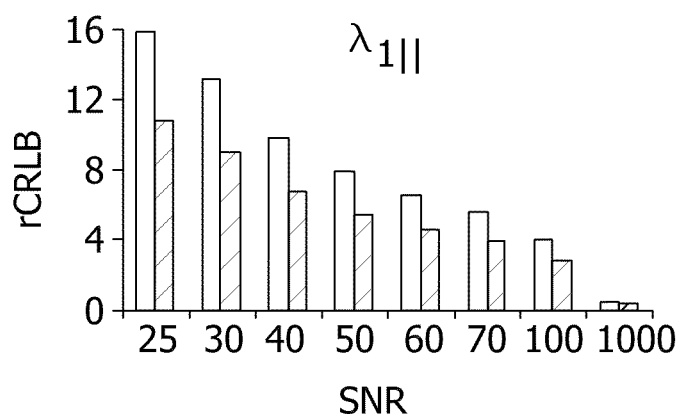
FIG. 37A is a graph of an axial diffusivity $\lambda 1\parallel$ of a first fiber.
Figure 37B:
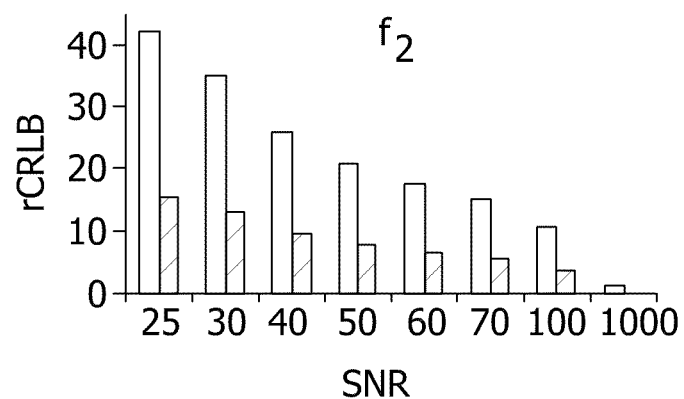
FIG. 37B is a graph of a volume ratio f2 of a second fiber.
Figure 37C:
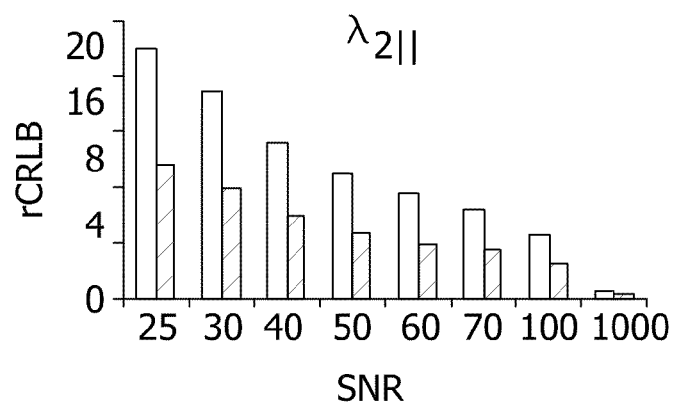
FIG. 37C is a graph of axial diffusivity $\lambda 2\parallel$ of the second fiber.
Figure 37D:
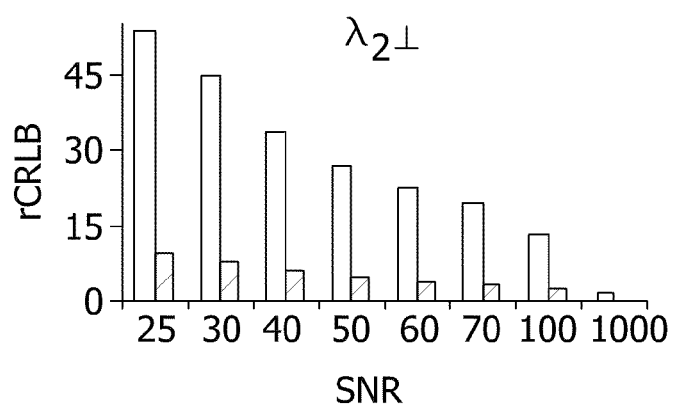
FIG. 37D is a graph of radial diffusivity $\lambda 2^\perp$ of the second fiber.

To further demonstrate the capability of DBSI to resolve multiple crossing fibers, a 3-fiber crossing phantom was built using fixed mouse trigeminal nerves arranged in an approximate equilateral triangle with inner angles of (a/b/c)=(75°/55°/50°, as is shown in FIG. 36.

Figure 22:
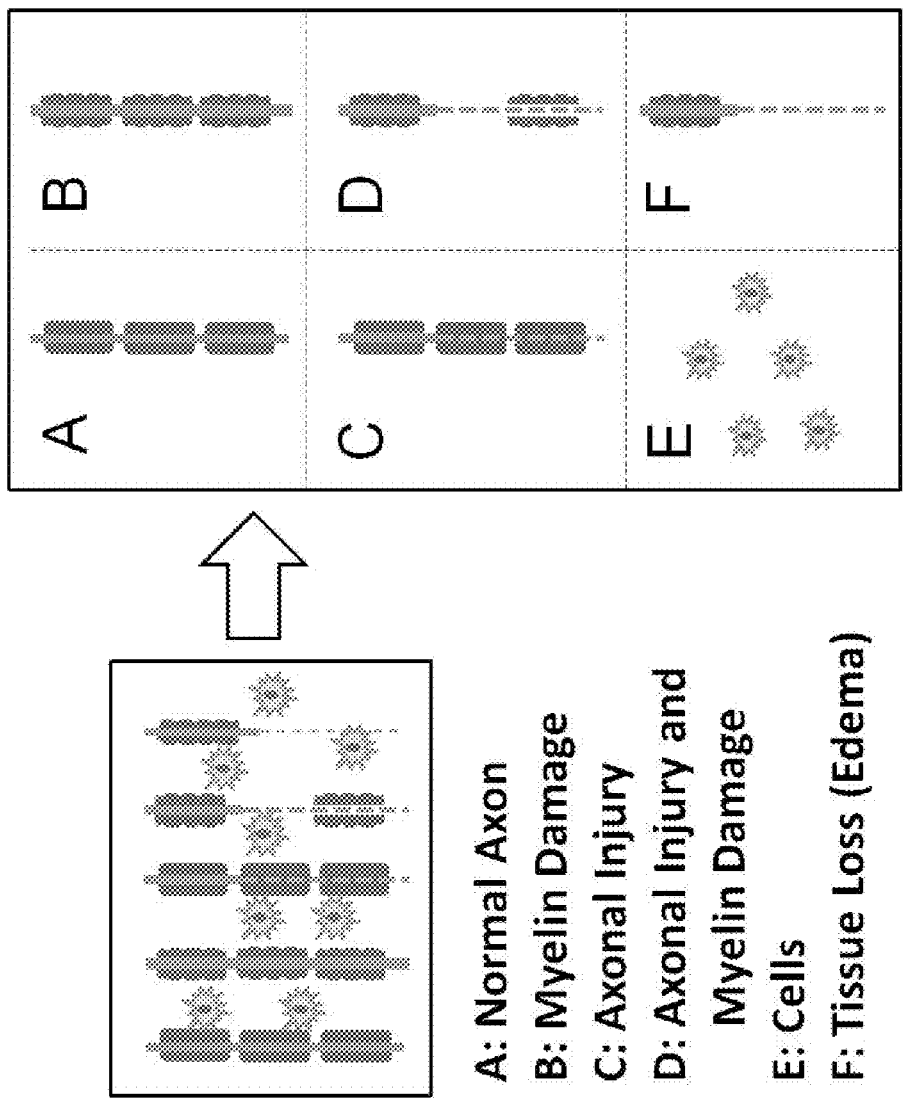
FIG. 22 is an illustration of heterogeneous pathology within one image voxel of interested white matter lesion.
Figure 40:
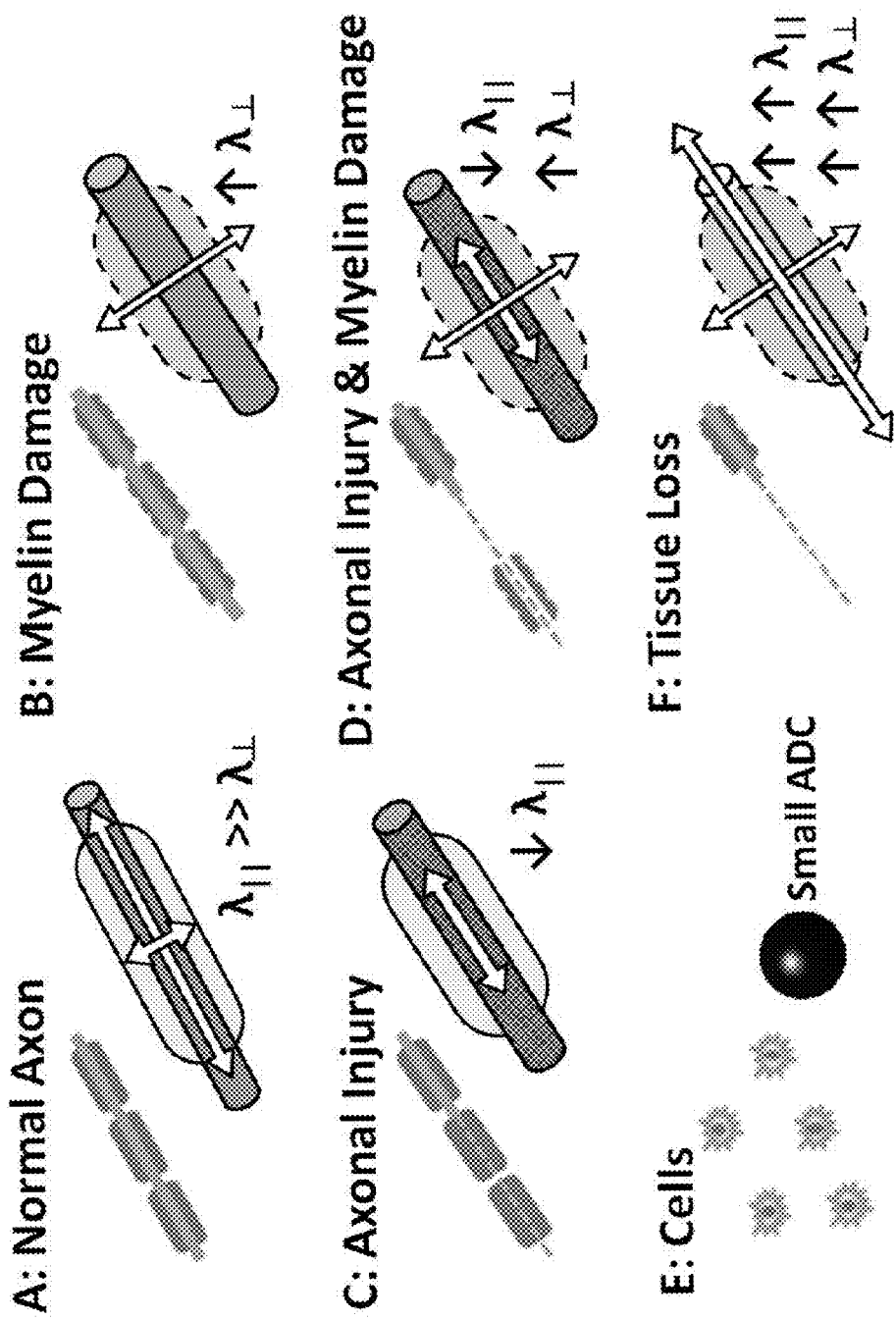
FIG. 40 is an illustration of the DTI signature of homogeneous pathologies.

Based on DBSI-derived number of fibers and the associated fiber principle orientations (Eq. [2]), the detailed composition of each nerve bundle can be further estimated and classified according to the structure and/or pathology (FIG. 22). Homogenous pathologies in a coherent white matter tract bundle exhibit a unique signature of DTI-derived directional diffusivities (FIG. 40). To demonstrate the effect of complex pathologies, spinal cord white matter, a simple nerve bundle without fiber crossing, was examined. To properly model spinal cord white matter lesions containing heterogeneous and co-existing pathologies (FIG. 41), we model diffusion weighted MR signal as a linear combination of a series of anisotropic diffusion tensors (representing heterogeneous axon fibers with different pathology) plus a spectrum of isotropic diffusion components (representing inflammation associated cell infiltration and edema, or tissue loss), Eq. [5]:

$$S_k = \sum_{i=1}^{M}\sum_{j=1}^{N} f_{ij} e^{-|\vec{b}_k|\lambda_{\perp\_i}} e^{-|\vec{b}_k|\cdot(\lambda_{\|\_i}-\lambda_{\perp\_i})\cos^2\theta_k} + \sum_{p=1}^{N} h_p e^{-|\vec{b}_k|\lambda_p}$$

(Equation 5)

Figure 23:
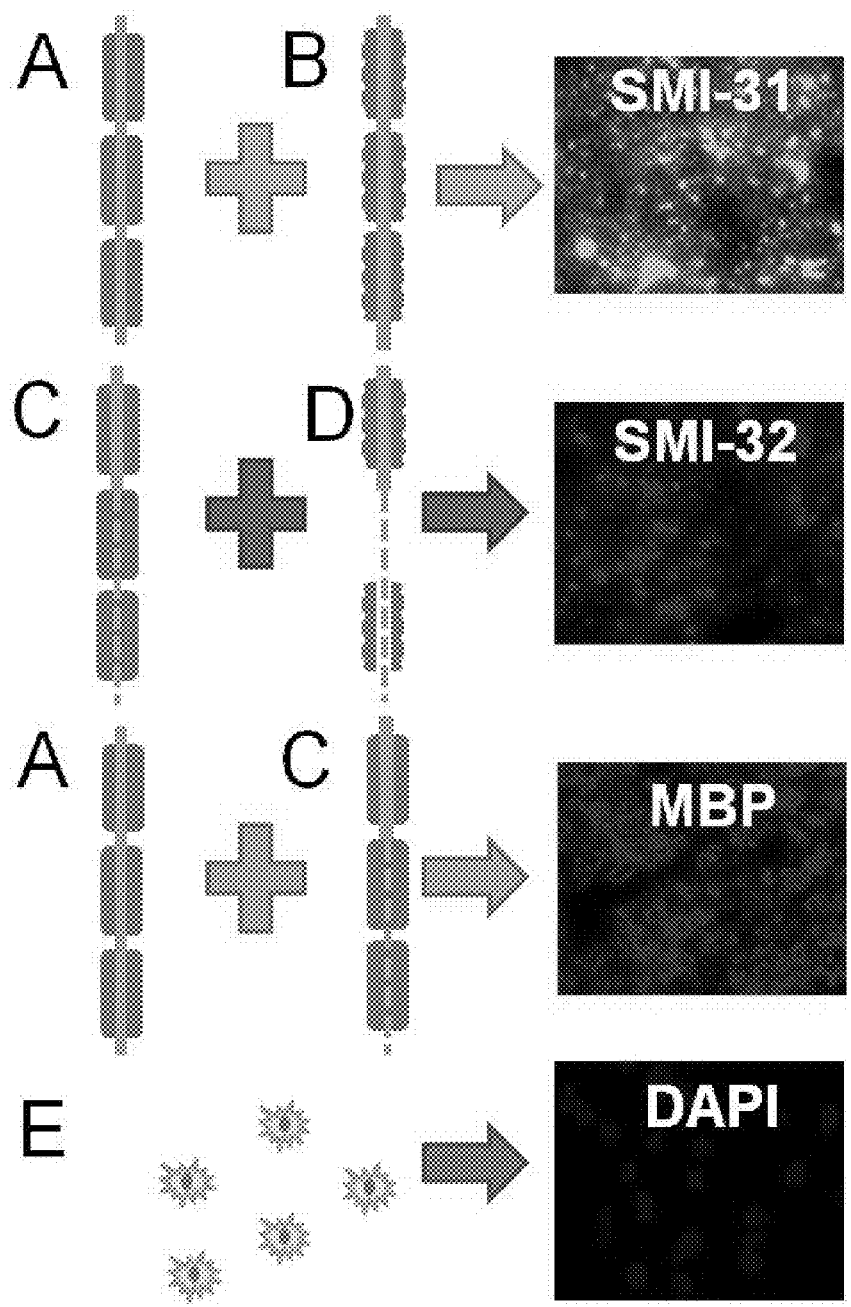
FIG. 23 is an illustration of conventional invasive histology.
Figure 24A:
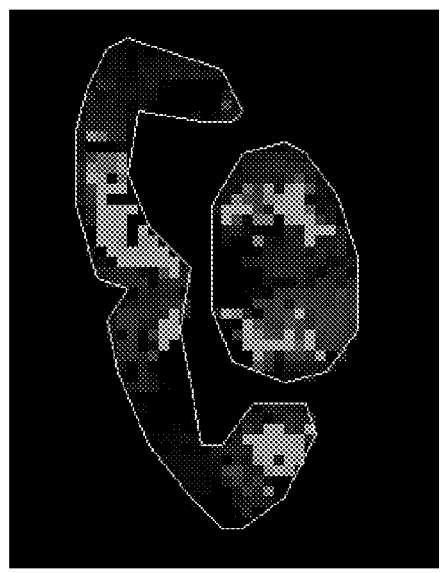
FIG. 24A is a detailed view of the DBSI-derived MBP fraction of the scan of FIG. 22.
Figure 24B:
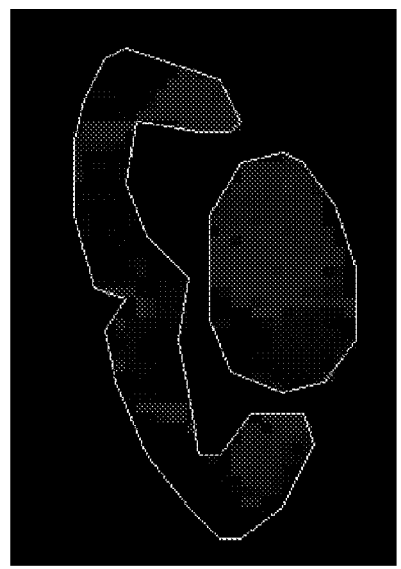
FIG. 24B is a detailed view of the DBSI-derived SMI-31 fraction of the scan of FIG. 22.
Figure 24C:
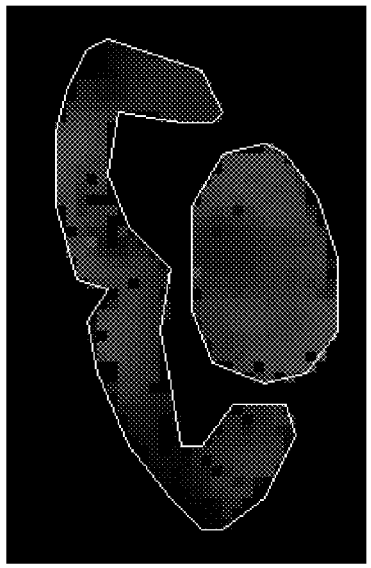
FIG. 24C is a detailed view of the DBSI-derived DAPI fraction of the scan of FIG. 22.
Figure 24D:
FIG. 24D is a detailed view of the DBSI-derived water fraction of the scan of FIG. 22.
Figure 25:
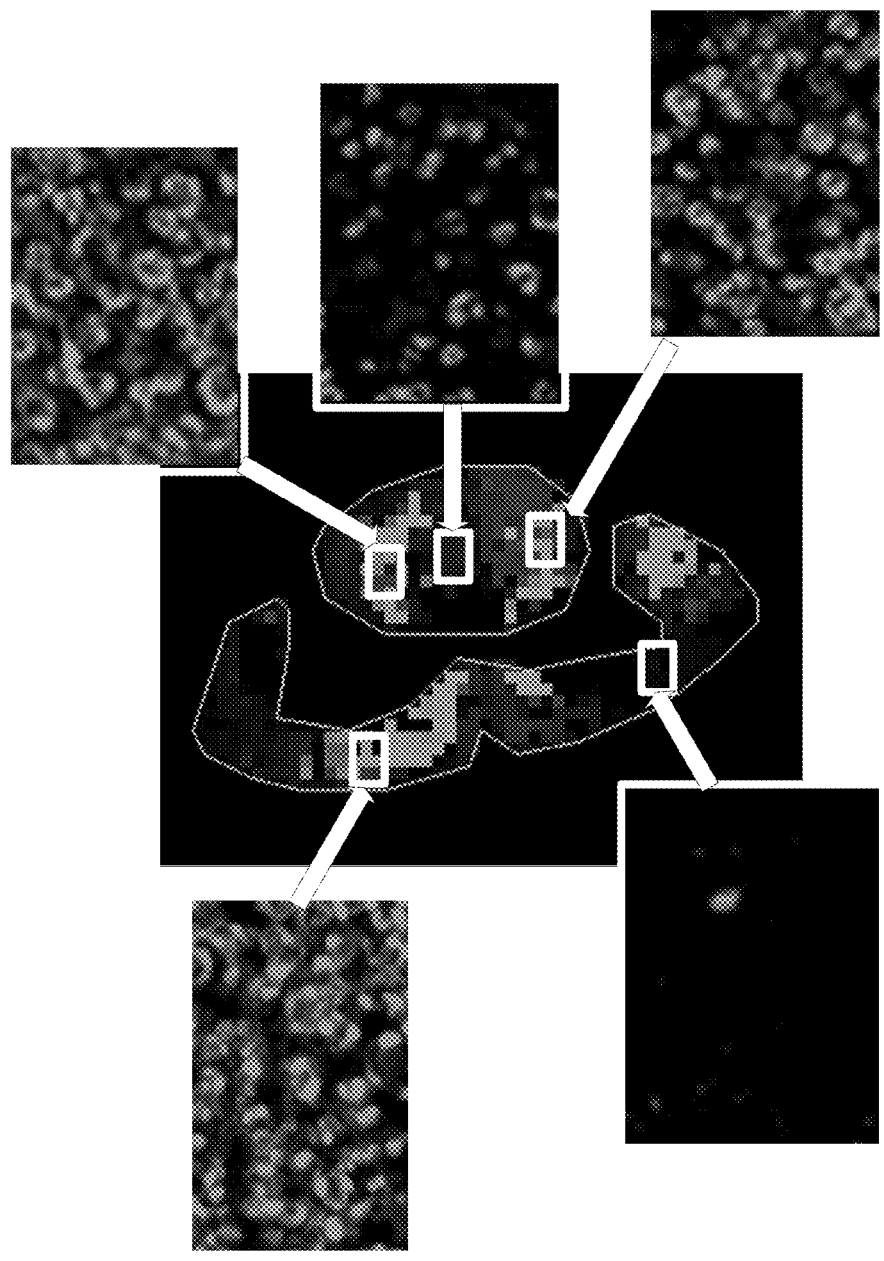
FIG. 25 is a detailed view of the DBSI-derived MBP fraction of the scan of FIG. 22 in the center surrounded by conventional invasive histology images from five selected regions.
Figure 26:
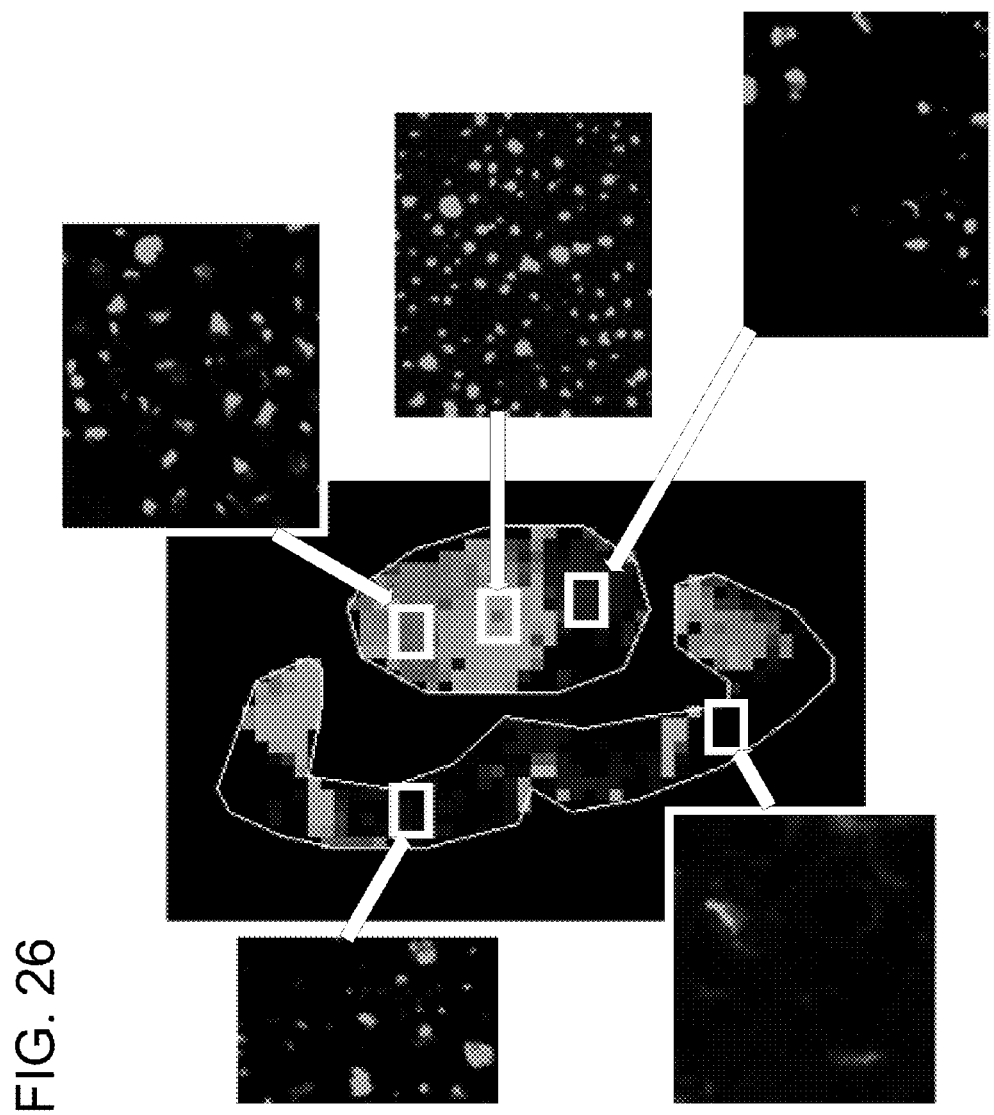
FIG. 26 is a detailed view of the DBSI-derived SMI-31 intensity of the scan of FIG. 22 in the center surrounded by conventional invasive histology images from five selected regions.
Figure 27:
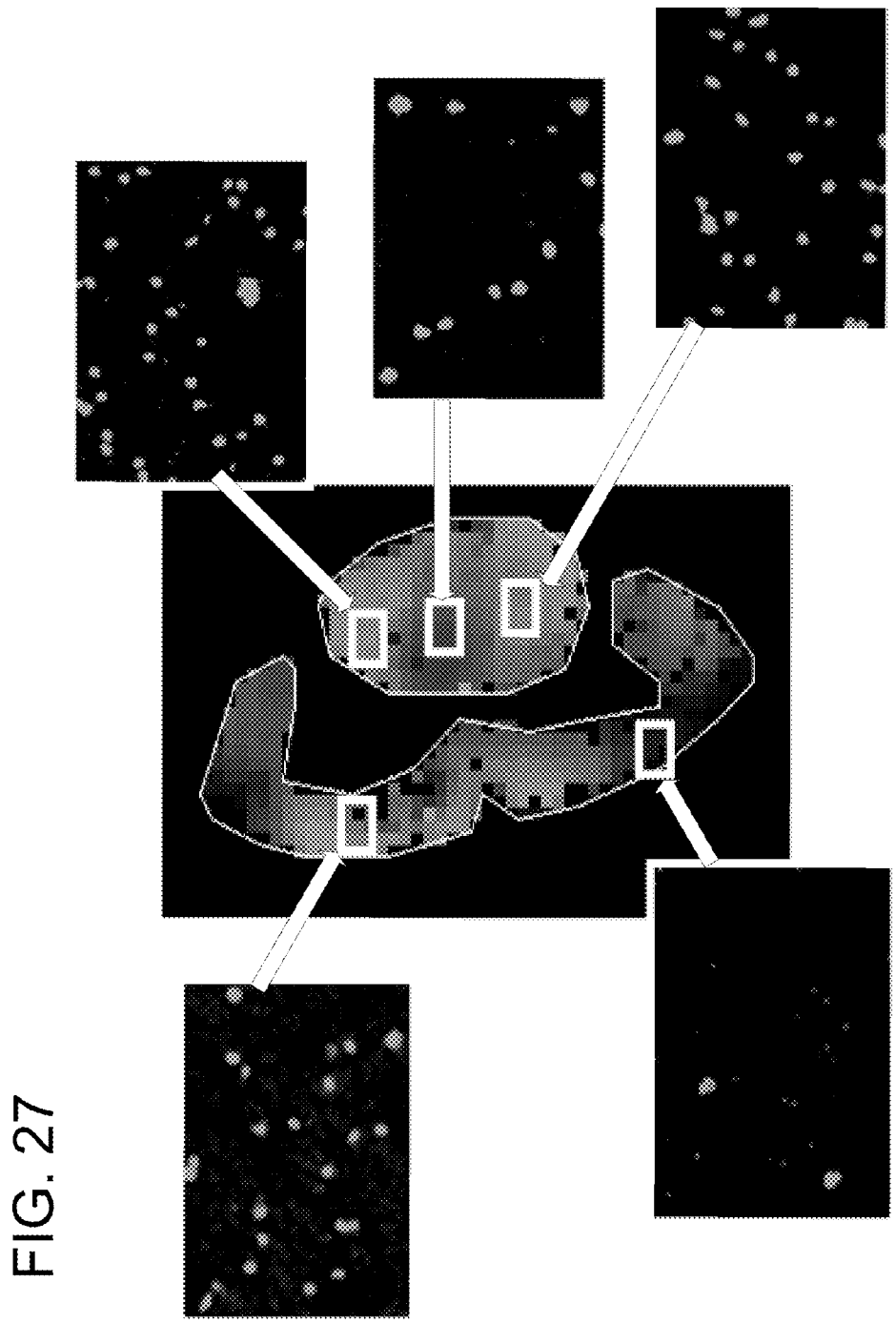
FIG. 27 is a detailed view of the DBSI-derived DAPI intensity of the scan of FIG. 22 in the center surrounded by conventional invasive histology images from five selected regions.
Figure 41:
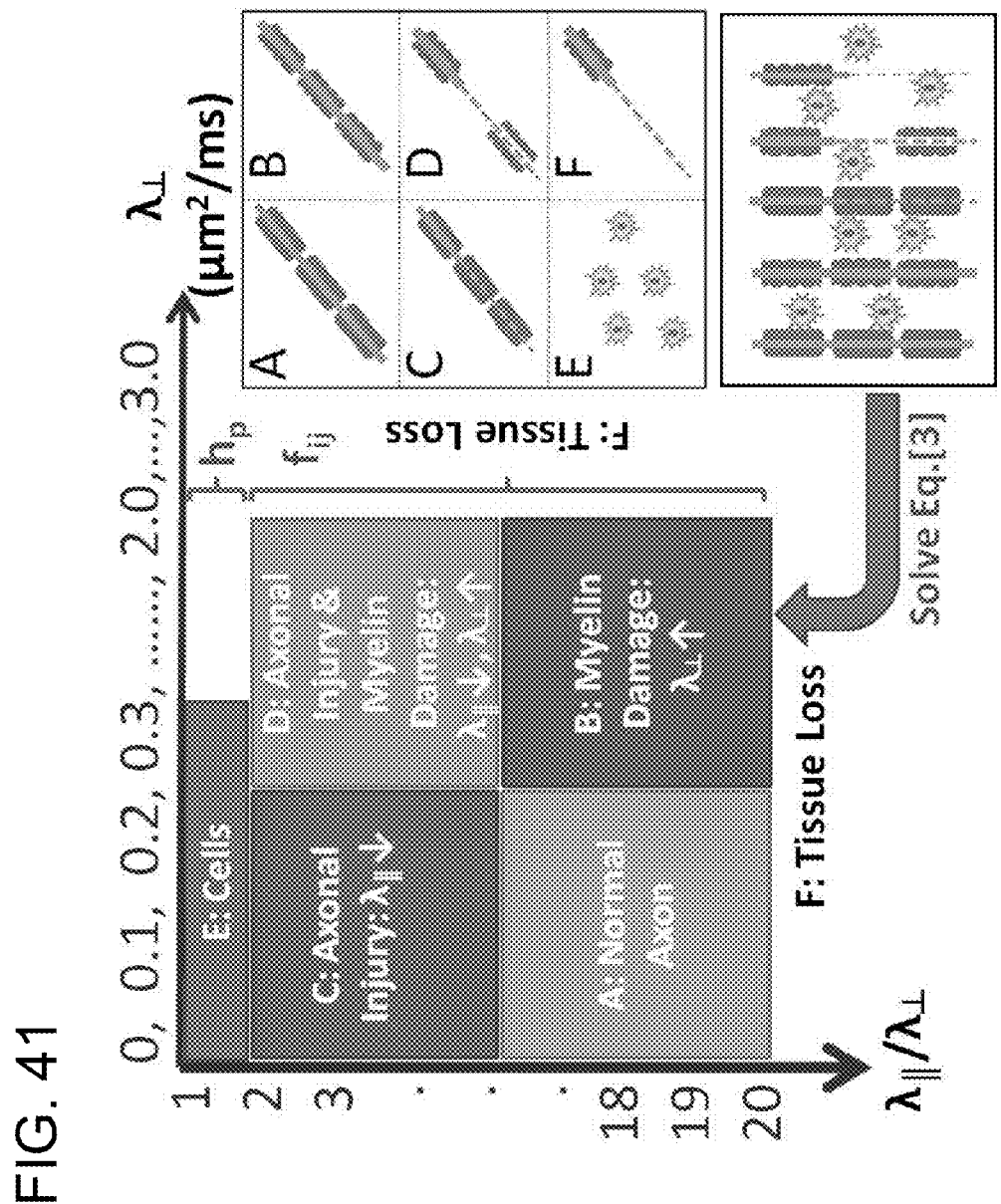
FIG. 41 is an illustration of the procedure to calculate individual pathology maps.

$f_{ij}$ is the non-diffusion weighted signal intensity fraction of the anisotropic tensor delineated by ($\lambda_{\perp\_i}$, $\lambda_{\|\_j}$). As demonstrated by the schematic plot in FIG. 41, $\lambda_{\perp\_i}$ are the $i^{th}$ (i=1, 2, ..., M) radial diffusivity uniformly distributed within the limits of [0,2] (μm²/ms); $\lambda_{\|\_j}$ are the $j^{th}$ (1, 2, ..., N) axial diffusivity uniformly discretized within the limits of [1.1, 20]×$\lambda_{\perp\_i}$. M×N is the total number of possible anisotropic tensor types distributed within physiological and pathological ranges, which can be classified into five groups: (A) normal axon; (B) demyelinated axon (increased $\lambda_{\perp\_i}$, and unchanged $\lambda_{\|\_j}$); (C) injured axon (unchanged $\lambda_{\perp\_i}$, and decreased $\lambda_{\|\_j}$); (D) injured axon with demyelination (increased $\lambda_{\perp\_i}$, and decreased $\lambda_{\|\_j}$), and (F) tissue loss (significantly increased $\lambda_{\|}$ or $\lambda_{\perp\_j}$). Mean−2×STD of DBSI-derived $\lambda_{\|}$ on normal spinal cord white matter is used as threshold to define the decreased $\lambda_{\|\_j}$; $\lambda_{\|\_j}$>Mean−6×STD indicates significant $\lambda_{\|\_j}$ increase. Similarly, Mean+2×STD of DBSI-derived $\lambda_\perp$ is used as threshold to define the increased $\lambda_{\perp\_j}$. $h_p$ is the non-diffusion weighted signal intensity fraction of the $p^{th}$ (p=1, 2, ..., H) isotropic tensor with mean diffusivity $\lambda_p$ uniformly distributed within the range of [0,3] (μm²/ms). In the present pilot study, a diffusion-weighting scheme with K=100 distinct b-values and directions uniformly distributed on 3D Cartesian grid was employed. The detailed composition of the spinal cord white matter described by $f_{ij}$ together with the isotropic diffusion spectrum described by $h_p$ is determined by solving equation [5] through a regularized nonnegative least-squares (NNLS) analysis (FIG. 41). The a priori information of nonnegative signal intensity and smooth signal intensity distribution is incorporated as penalty terms to effectively prevent the NNLS from over-fitting the measured noisy data while retaining the numerical accuracy of the solution. Based on the results of the second step, the non-diffusion weighted signal intensity fraction ($f_{ij}$) of the anisotropic tensors belonging to each group were summed up to compute individual pathology component map (FIG. 41): (Map A) the normal axon density; (Map B) demyelinated axon density; (Map C) injured axon density; (Map D) injured and demyelinated axon density; and (Map F) density map of tissue loss. Isotropic diffusion component (Map E) was computed as the summation of fractions from all the isotropic components ($h_p$). The classic immunohistochemical SMI-31+ staining for the intact axons was approximated by the summation of maps A and B (FIG. 23); SMI-32+ map (staining for injured axons) by the summation of maps C and D (FIG. 23); MBP+ map (staining for axons with intact myelin) by the summation of maps A and C (FIG. 23); DAPI+map (staining for cell nucleus) by map E (FIG. 23). Exemplary results from this operation are shown in FIGS. 24-27.

A SNR dependent Monte Carlo simulation and a Cramér-Rao Lower Bound (CRLB) analysis on a model (two crossing fibers with one non-restricted isotropic component) and diffusion scheme (three-fold tessellated icosahedric gradient directions, 184 total directions, on two shells: b1/b2=1000, 3500 s/mm²) was performed. FIGS. 37A-37D illustrate the relative CRLB (rCRLBfor axial diffusivities ($\lambda 1\|$, $\lambda 2\|$) of both fibers, and the volume ratio (f2) and radial diffusivity ($\lambda 2^\perp$) of the second fiber as a function of SNR.

Figure 38A:
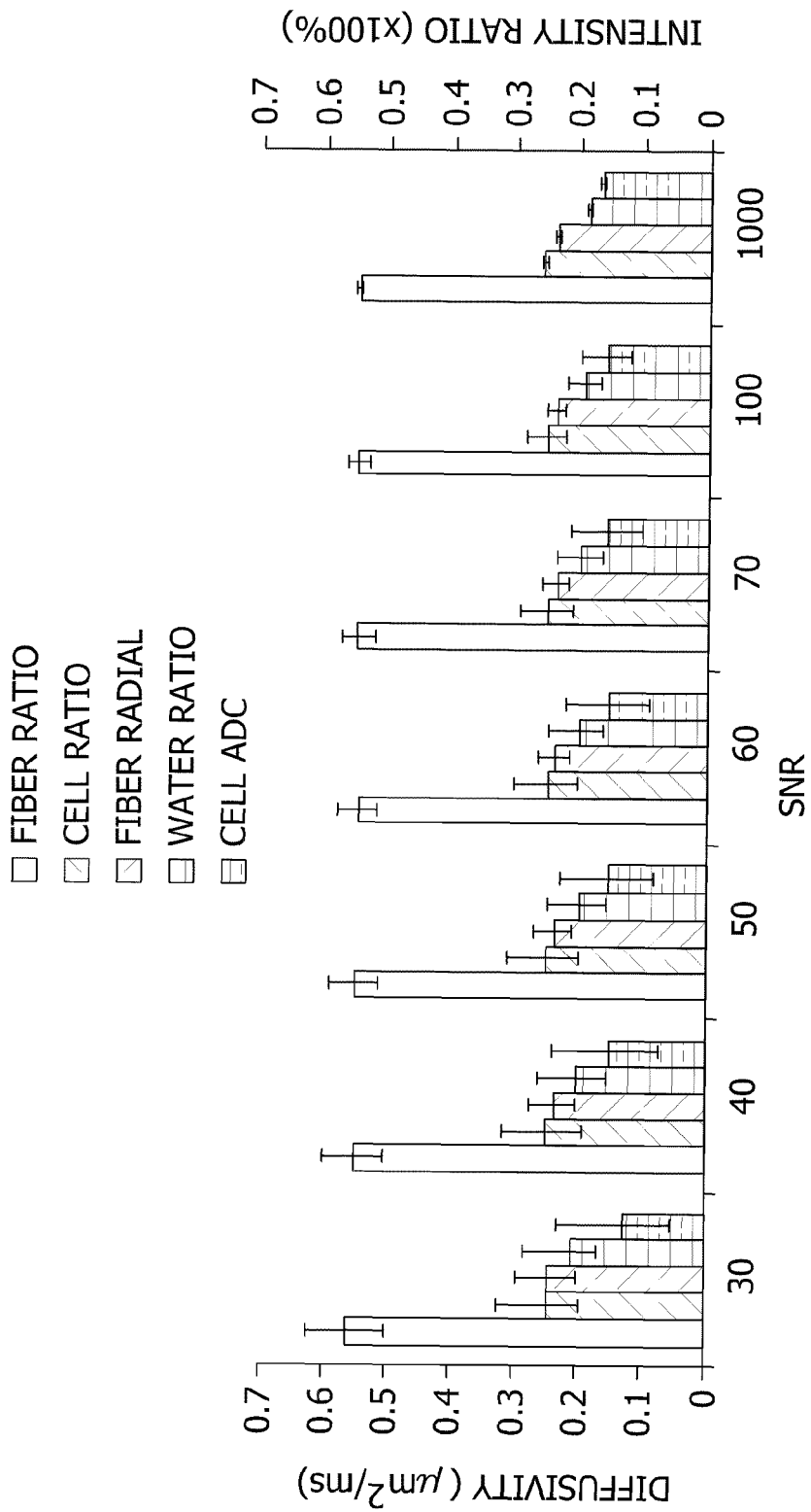
FIG. 38A is an MC-simulation-derived graph displaying fiber ratio, water ratio, cell ratio, cell ADC, and fiber radial diffusivity of diffusion MRI data generated in silico.
Figure 38B:
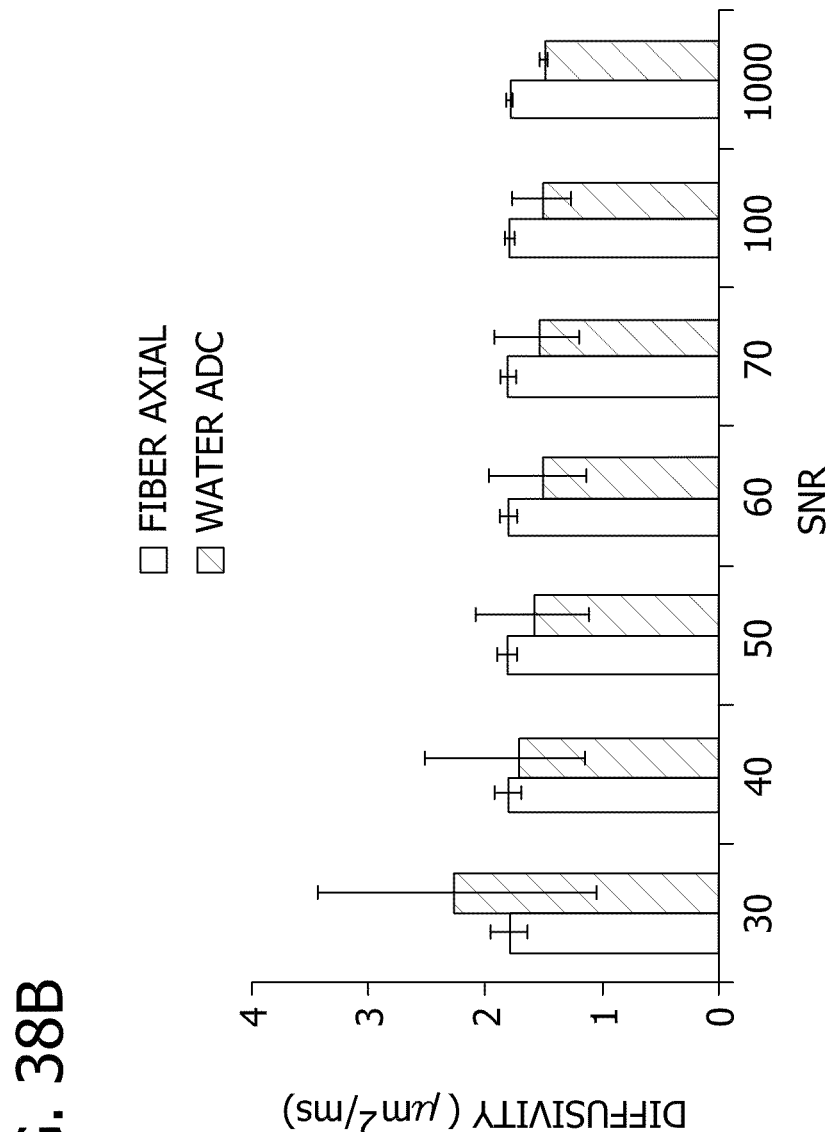
FIG. 38B is an MC-simulation-derived graph displaying fiber axial diffusivity, water ADC of diffusion MRI data generated in silico.

FIGS. 38A and 38B are graphs pertaining to diffusion MRI data representative of a single-fiber with restricted isotropic diffusion and nonrestricted isotropic diffusion were generated in silico via Monte Carlo simulations. The in silico generated data mimicked in vivo mouse spinal cord white-matter diffusion properties at the peak of EAE: single fiber (white-matter tract, $\lambda\|$=1.8 μm²/ms, $\lambda^\perp$=0.24 μm²/ms, along z direction, fiber fraction 55%), restricted isotropic component (infiltrating cells, ADC=0.17 μm²/ms, cell fraction 26%), and nonrestricted isotropic component (edema, ADC=1.8 μm²/ms, 19%). All model parameters were estimated accurately at SNR=40, typical of our in vivo mouse spinal-cord measurements, with bias <15%. MC simulation and CRLB derived variances agreed with each other, and improved with SNR. These results confirm that DBSI-derived diffusion parameters have sufficient precision to permit meaningful estimates of fiber ratio, water ratio, cell ratio, cell ADC, and fiber diffusivities in mice in vivo.

Figure 39:
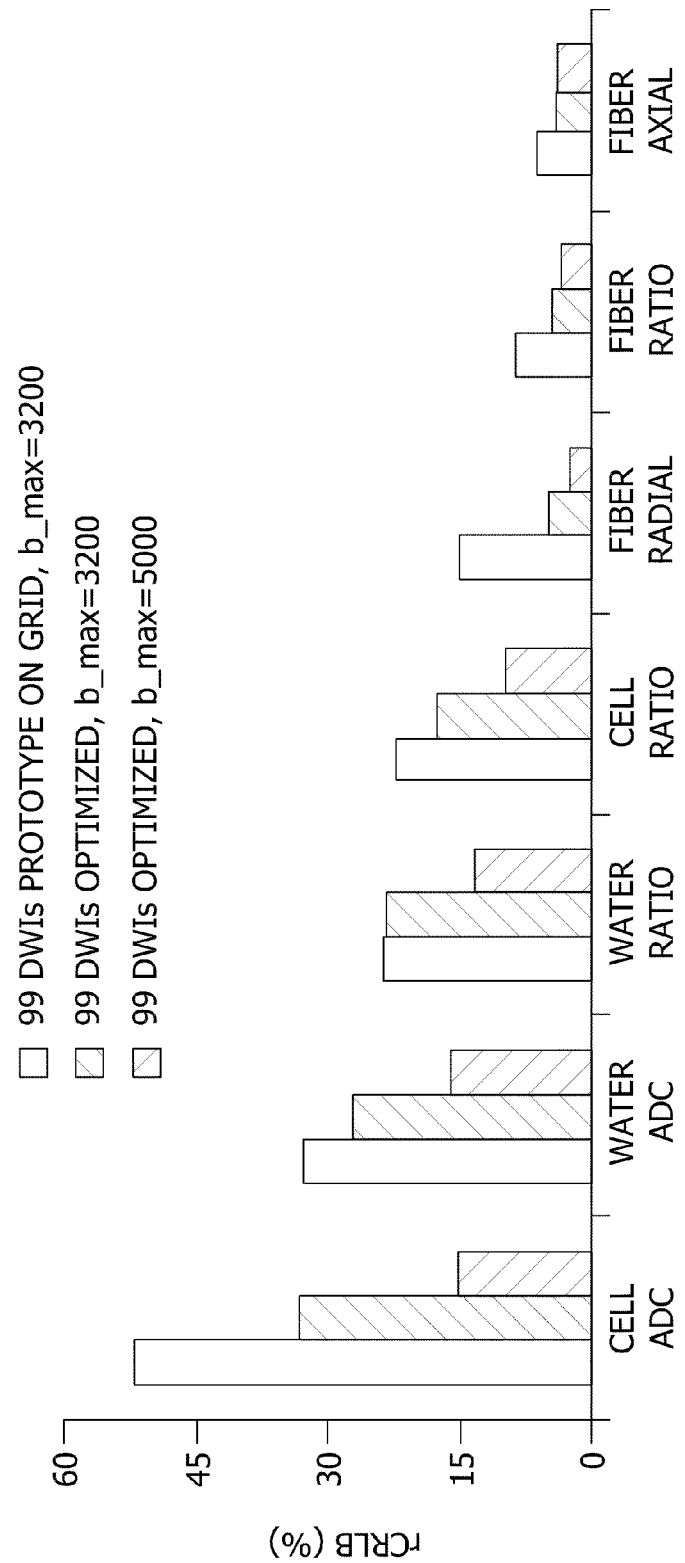
FIG. 39 is a CRLB based optimization of a one-fiber and a two-isotropic compartments diffusion model.

Results suggest that with CRLB optimization at the same max b-value the precision can be improved by optimizing diffusion directions (~40% improvement vs. the prototype DBSI). The optimized directions with increased max b-value (=5000) yielded ~140% improvement over the prototype DBSI (b-value in s/mm²), as is shown in FIG. 39.

Figure 42:
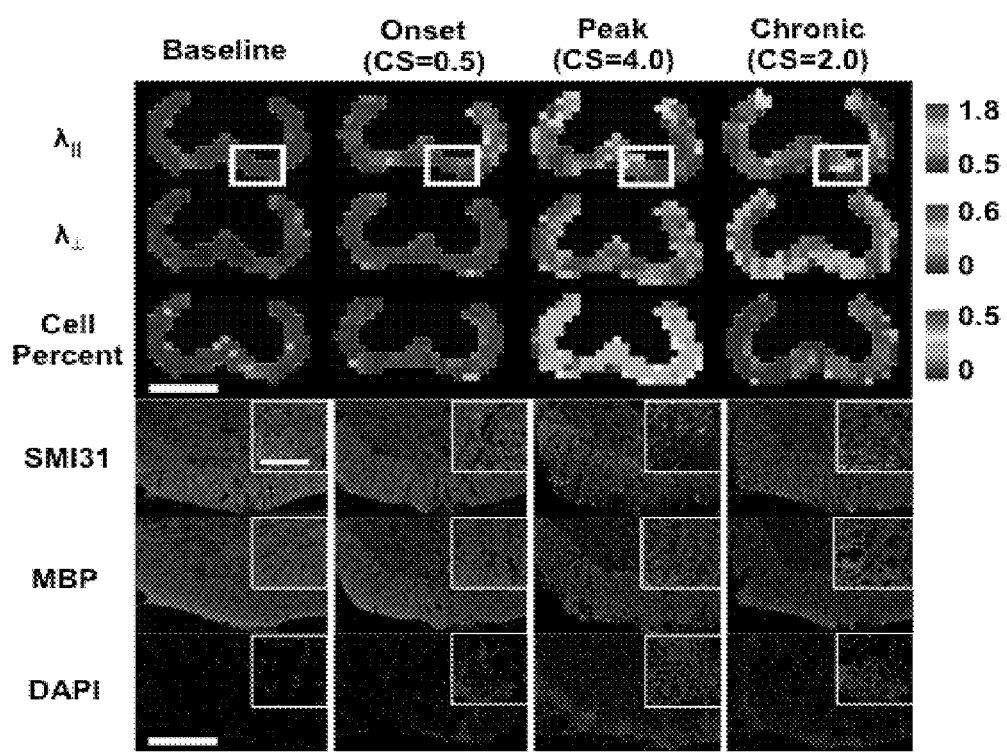
FIG. 42 is an illustration of in vivo DBSI derived $\lambda\parallel$, $\lambda^\perp$, and cell fraction maps of mice from each time point are displayed with the corresponding axon (SMI-31), myelin (MBP), and nucleus (DAPI) staining.
Figure 43:
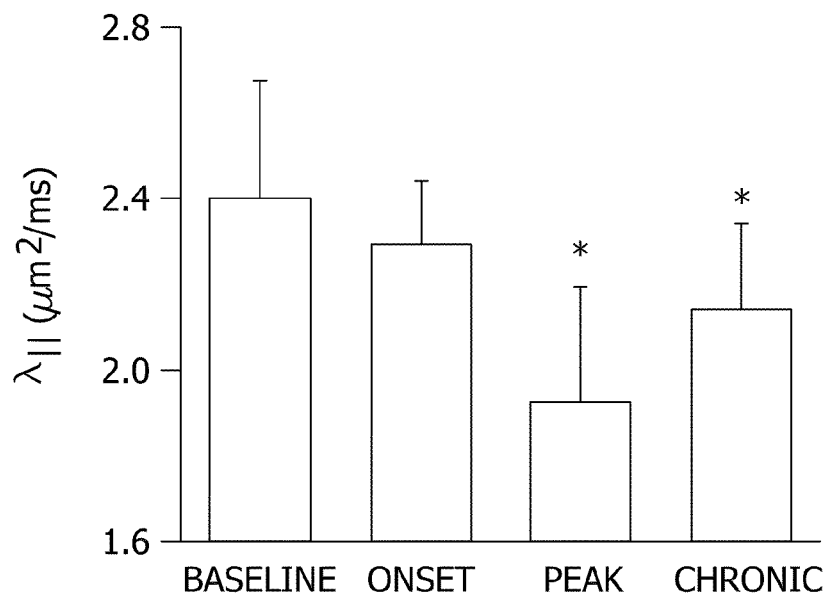
FIG. 43 is a cross-sectional time course of in vivo DBSI derived $\lambda\parallel$ from B6-EAE mice at baseline (control), onset, peak, and chronic disease states.
Figure 44:
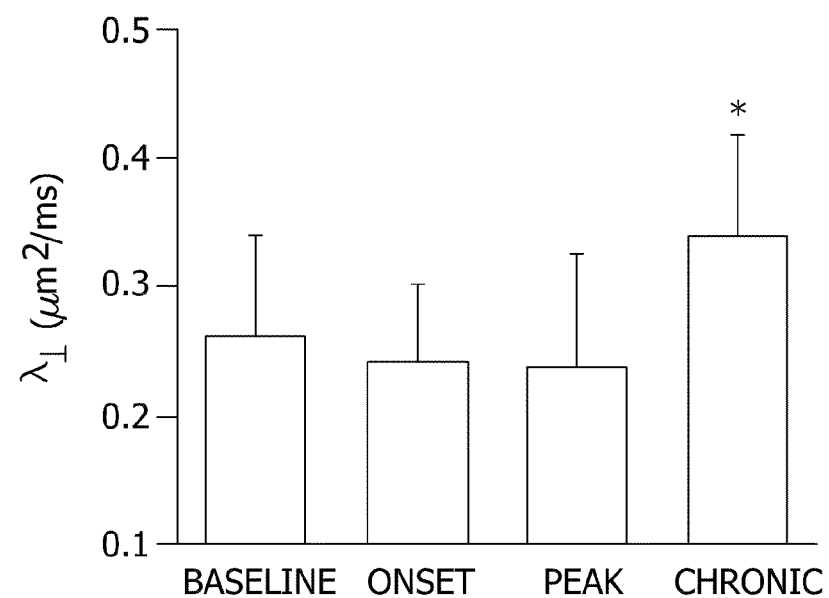
FIG. 44 is a cross-sectional time course of in vivo DBSI derived $\lambda^\perp$ from B6-EAE mice at baseline (control), onset, peak, and chronic disease states.

A cross-sectional study was performed on 20 B6-EAE mice spinal cords at baseline (control), onset, peak, and chronic states, followed by IHC (N=5 for each time point). In the representative mouse, $\lambda_\parallel$ decreased at the peak and recovered slightly at the chronic EAE stage, consistent with decreased SMI-31 staining followed by the recovery of the staining as is shown by FIGS. 42 and 43. Increased $\lambda_\perp$ was seen at EAE peak and continued to increase to the chronic EAE stage, consistent with the MBP staining gradually losing its intensity FIGS. 42, and 44.

Figure 45:
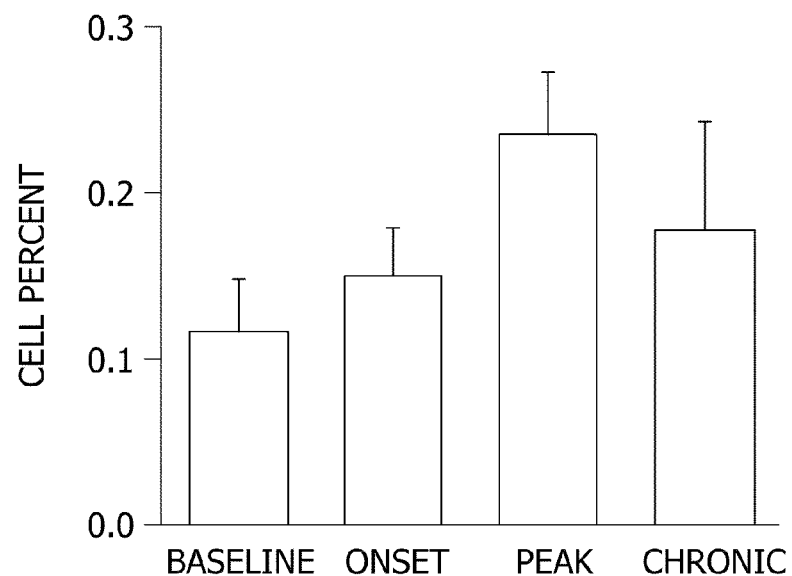
FIG. 45 is a cross-sectional time course of in vivo DBSI derived cell intensity percentage from B6-EAE mice at baseline (control), onset, peak, and chronic disease states.
Figure 46:
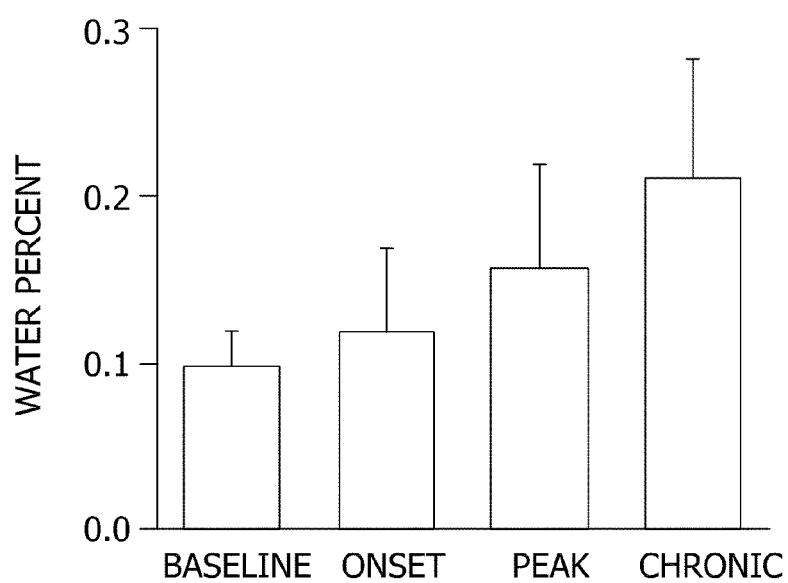
FIG. 46 is a cross-sectional time course of in vivo DBSI derived water intensity percentage from B6-EAE mice at baseline (control), onset, peak, and chronic disease states.

DBSI revealed cell infiltration at peak EAE, consistent with DAPI staining and clearly indicating the presence of inflammation (FIGS. 42 and 45). Quantitative analysis of the ventrolateral white matter DBSI parameters closely reflects the same pathology profile suggested by IHC shown in FIGS. 43-46. DBSI reflects axon and myelin injury more accurately than that previously determined by DTI, and correctly depicts inflammatory pathological features of the spinal cord white matter from EAE mice in terms of both cell infiltration and vasogenic edema as shown in FIGS. 45 and 46.

A segment of autopsy cervical spinal cord, fixed in 10% formalin, from 54 years old Caucasian female with 22-year disease duration was examined on a 4.7-T preclinical MR scanner: Varian DirectDrive™ console, 15-cm inner diameter, actively shielded Magnex gradient coil (60 G/cm, 270 μs rise time). Tissue contained in a 3-ml syringe with 10% formalin was placed in a custom-made solenoid coil for data acquisition using the following parameters: TR 2 s, TE 39 ms, Δ 20 ms, δ8 ms, slice thickness 0.5 mm, number of slices 5, field-of-view 2.4×2.4 cm2, number of averages 1, data matrix 192×192.

Figure 47:
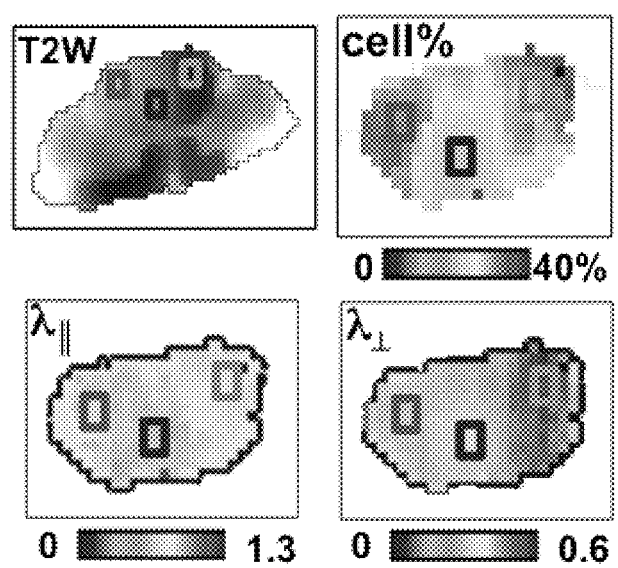
FIG. 47 is an ex vivo DBSI of a human MS autopsy spinal cord specimen.
Figure 48:
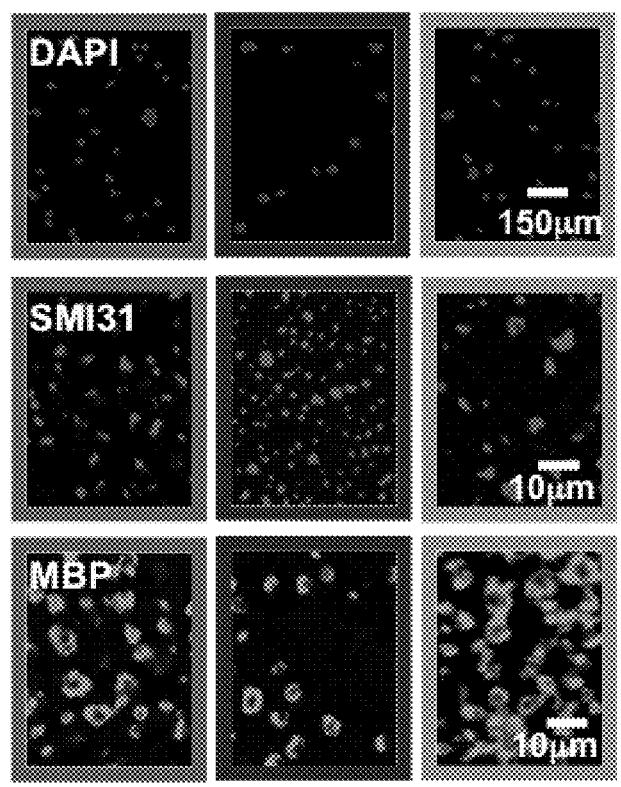
FIG. 48 is an ex vivo histology images of a human MS autopsy spinal cord specimen.
Figure 49:
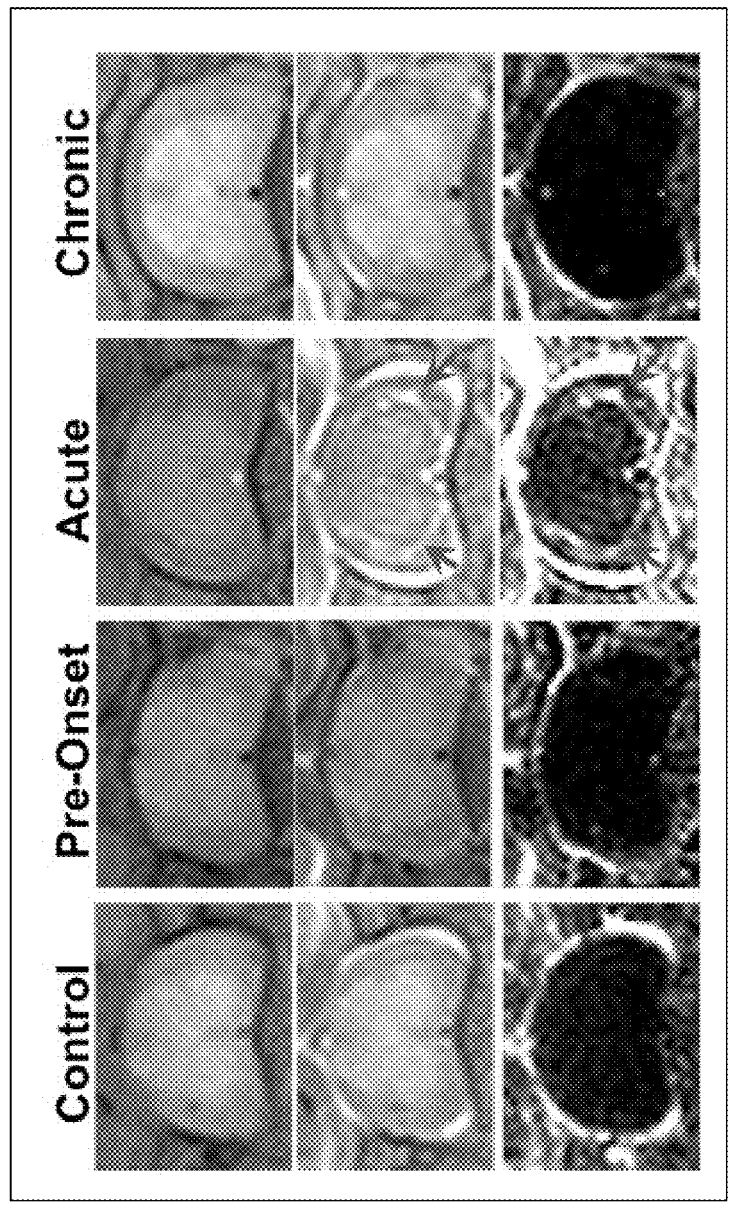
FIG. 49 is T1W MRI of mouse spinal cords.
Figure 50:
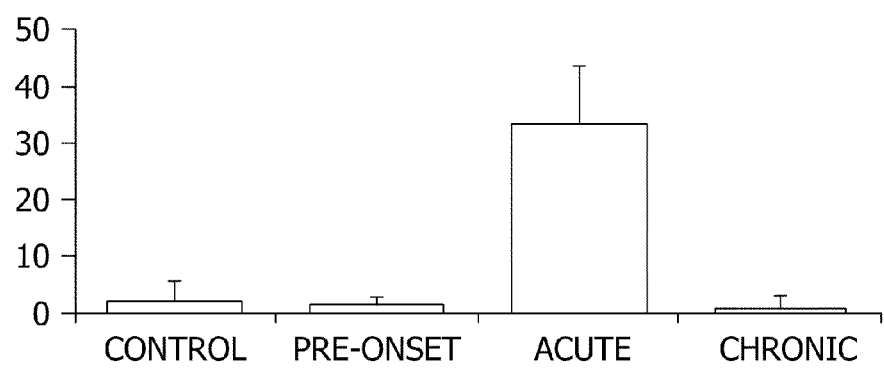
FIG. 50 is a quantitative analysis of percentage enhancement map of FIG. 49.

Diffusion sensitizing gradients were applied in 99 directions with max b-value=3200 s/mm². In plane resolution was 125×125 μm². DBSI/DTI maps were coregistered with IHC images and an ROI analysis was employed after co-registration of MRI and IHC images as shown in FIGS. 47 and 48. Diffuse white-matter injury was present in the dorsal column, consistent with the recorded upper extremity numbness of this patient. Significantly increased cell infiltration was seen in all three ROIs, consistent with DAPI staining. The effect of infiltrating cells on diffusion is evident by examining DTI-derived $\lambda_\parallel$ at (0.36±0.02 μm²/ms) and (0.31±0.01 mm²/ms; total 16 image voxels, p=0.07) from the left and right ROI of the dorsal column, where more cell infiltration was noted. In contrast, DBSI-derived $\lambda_\parallel$ at the left (0.81±0.03 mm2/ms) and right (0.74±0.03 mm2/ms; total 16 voxels, p=0.0005) ROI was significantly different, revealing more axonal injury at the right ROI, consistent with the SMI-31 staining. Similarly, DBSI-derived $\lambda_\perp$ reveals that the severity of demyelination is again consistent with the MBP staining. This co-registered ROI analysis confirms that DBSI is consistent with IHC findings (FIGS. 47 and 48).

Spherical Harmonic Decomposition (SHD) has been proposed as a method for classifying imaging voxels into isotropic, single-, and multi-fiber components based on SHD coefficients. However, SHD cannot accurately estimate the intra-voxel fiber numbers, fiber volume fractions, fiber anisotropy, or fiber orientations. Even in the simple case of two fibers, it is not possible to use SHD to uniquely determine the intra-voxel fiber numbers and orientation since both the volume fraction and relative fiber orientations interfere with the higher order SHD components in a similar fashion. Similar to DSI, SHD also requires high diffusion weighting gradients. In contrast, DBSI facilitates separating and quantifying the isotropic and individual anisotropic (fiber) components while maintaining the use of low diffusion weighting gradient magnitudes.

Q-ball imaging of the human brain is a method closely related to DSI. In DSI, the ODF is reconstructed by sampling the diffusion signal on a Cartesian grid, Fourier transformation, followed by the radial projection. Q-ball imaging acquires the diffusion signal spherically and reconstructs the ODF directly on the sphere. The spherical inversion is accomplished with the reciprocal space funk radon transform (FRT), a transformation of spherical functions that maps one function of the sphere to another. Q-ball and DSI are theoretically equivalent and generate similar ODF. However, q-ball methods are not capable of estimating fiber angles as well as quantifying multiple tensor parameters.

Independent Component Analysis (ICA) has been proposed for application in DTI tractography to recover multiple fibers within a voxel. Although the angle of crossing fibers within voxels can be estimated to within 20 degrees of accuracy, eigenvalues cannot be recovered to obtain the complete tensor information such as the Fractional Anisotropy (FA).

Moreover, it has been proposed to use a high angular resolution diffusion imaging (HARDI) data set as a method that is capable of determining the orientation of intra-voxel multiple fibers. For example, up to 2 fiber components and one isotropic component may be considered. Similar to DBSI, HARDI methods have employed a mixed Gaussian model incorporating the isotropic diffusion component. However, HARDI is very different in nature compared with DBSI. For example, (i) HARDI fails in voxels with more than 2 fibers; (ii) HARDI does not work in voxels with more than 1 isotropic component, which is commonly seen in pathological conditions with both cell infiltration and edema; (iii) HARDI fails to compute isotropic diffusivity, improving fiber orientation estimation at the expense of removing the isotropic diffusion component; (iv) HARDI cannot compute the absolute axial and radial diffusivities for each component fiber; (v) HARDI cannot compute the true volume fractions of each fiber or isotropic component. In contrast, DBSI facilitates achieving all the goals enumerated above because it may be used to solve for issues that HARDI ignores or simplifies. HARDI-based methods have aimed to enhance the tools available for fiber tracking but do not compute the directional diffusivities of fibers, the isotropic diffusivity, or true volume fractions.

In summary, diffusion MRI methods in the field currently focus on determining the primary orientation of crossing fibers within one voxel. To achieve this goal, most have to relax the condition needed for accurate estimation of diffusivity or the volume ratio of individual component. DBSI facilitates not only resolving the primary direction of each fiber component, but also identifying and quantifying one or more other physical properties available from the diffusion measurements.

With the quantified fraction, axial diffusivity, and radial diffusivity of each fiber as well as the fraction and mean diffusivity of each isotropic diffusion tensor, CNS white matter pathology maps corresponding to the classic immunohistochemistry staining of excised tissues may be generated. For example, based on the axial diffusivity distribution intact (or injured) axonal fiber tract fraction may be estimated and the fraction distribution map may be generated to reflect the classic phosphorylated neurofilament (SMI-31, for intact axons), or dephosphorylated neurofilament (SMI-32, for injured axons), staining. The restricted isotropic diffusion component estimated using DBSI constitutes a map of cell distribution corresponding to nucleus counting using DAPI staining on the fixed tissue allowing a direct estimate the extent of inflammation in patient CNS white matter.

In this disclosure, we have developed a method incorporating the diffusion profile of each component within the image voxel to perform the tissue classification based on the raw diffusion MRI data. This is a novel approach that has never been demonstrated previously. The typical classification is performed using the generated parameters, not the source data. Our approach generates realistic "noninvasive histology" maps of various CNS white matter pathologies directly related to the actual immunohistochemistry staining that is only available after tissue excision and fixation. Although an accurate assessment of the underlying white matter pathologies may or may not correctly reflect clinical symptoms during the early phase of the disease, it would likely predict the long-term patient disability. Such a quantitative assessment of CNS white matter tracts integrity would enable a patient based intervention clinically. For example, current MS treatments follow a standard dosing regimen, with limited opportunity to adjust management for individual patient responses. By quantitatively distinguishing and tracking inflammation, and axon and myelin injury, DBSI will provide the opportunity for efficacy assessment of disease-modifying interventions and allow treatment planning to reflect individual patient response.

Exemplary embodiments of methods, systems, and apparatus for use in diffusion basis spectrum imaging are described above in detail. The methods, systems, and apparatus are not limited to the specific embodiments described herein but, rather, operations of the methods and/or components of the systems and/or apparatus may be utilized independently and separately from other operations and/or components described herein. Further, the described operations and/or components may also be defined in, or used in combination with, other systems, methods, and/or apparatus, and are not limited to practice with only the systems, methods, and apparatus described herein.

A computer or processor, such as those described herein, includes at least one processor or processing unit and a system memory. The computer or processor typically has at least some form of computer readable media. By way of example and not limitation, computer readable media include computer storage media and communication media. Computer storage media include volatile and nonvolatile, removable and non-removable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Although the present invention is described in connection with an exemplary imaging system environment, embodiments of the invention are operational with numerous other general purpose or special purpose imaging system environments or configurations. The imaging system environment is not intended to suggest any limitation as to the scope of use or functionality of any aspect of the invention. Moreover, the imaging system environment should not be interpreted as having any dependency or requirement relating to any one or combination of components illustrated in the exemplary operating environment. Examples of well known imaging systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program components or modules, executed by one or more computers or other devices. Aspects of the invention may be implemented with any number and organization of components or modules. For example, aspects of the invention are not limited to the specific computer-executable instructions or the specific components or modules illustrated in the figures and described herein. Alternative embodiments of the invention may include different computer-executable instructions or components having more or less functionality than illustrated and described herein. A software module or program module may reside in random access memory (RAM), flash memory, read-only memory (ROM), erasable programmable read-only memory (EPROM), electrically erasable programmable read-only memory (EEPROM), registers, hard disk memory, a removable disk, a CD-ROM, or any other form of computer-readable storage medium known in the art.

The order of execution or performance of the operations in the embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

It will be understood by those of skill in the art that information and signals may be represented using any of a variety of different technologies and techniques. For example, data, instructions, commands, information, signals, bits, symbols, and/or chips may be represented by voltages, currents, electromagnetic waves, magnetic fields or particles, optical fields or particles, or any combination thereof. Similarly, the various illustrative logical blocks, modules, circuits, and algorithm operations described herein may be implemented as electronic hardware, computer software, or a combination of both, depending on the application and the functionality. Moreover, the various logical blocks, modules, and circuits described herein may be implemented or performed with a general purpose computer, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Exemplary general purpose processors include, but are not limited to only including, microprocessors, conventional processors, controllers, microcontrollers, state machines, or a combination of computing devices.

When introducing elements of aspects of the invention or embodiments thereof, the articles "a," "an," "the," and "said" are intended to mean that there are one or more of the elements. The terms "comprising," including," and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for determining a diffusivity of each diffusion component of multiple diffusion components within one volume of a plurality of volumes within a tissue using diffusion magnetic resonance data representing the one volume, the method comprising:
    determining, by a processor, a quantity of fibers and a primary orientation of each fiber within the one volume by:
        projecting the diffusion magnetic resonance data onto a diffusion basis set comprising a plurality of diffusion bases with a constant axial diffusivity and a constant radial diffusivity, each diffusion basis further defined by a direction;
        iteratively adjusting at least one of the axial diffusivity, the radial diffusivity, and one or more volume ratios to minimize a fitting error between a measured diffusion weighted signal and a diffusion weighted signal estimated using the diffusion basis set; and
        selecting a total number of fibers comprising those diffusion bases with a volume ratio greater than a signal-to-noise threshold and determining the primary orientation of each fiber comprising the direction of each diffusion basis corresponding to each fiber;
    by the processor, calculating for each fiber a fiber axial diffusivity indicating a diffusion of water in the direction of that fiber and a fiber radial diffusivity indicating a diffusion of water perpendicular to the direction of that fiber by:
        constructing a multi-tensor model comprising the total number of fibers, each fiber characterized by the fiber axial diffusivity, the fiber radial diffusivity, the primary orientation, and the volume ratio of that fiber; and
        iteratively adjusting at least one of the fiber axial diffusivities and the fiber radial diffusivities to minimize a second fitting error between the measured diffusion weighted signal and a second diffusion weighted signal estimated using the diffusion basis set; and
    determining, by the processor, a detailed composition of the tissue to resolve an underlying tissue pathology, the detailed composition including at least one of the fibers, the primary orientation of each fiber, the fiber axial diffusivities, the fiber radial diffusivities, and the fiber volume.

2. A method in accordance with claim 1, further comprising:
    calculating by the processor at least one isotropic diffusivity by:
    defining an isotropic diffusion basis set comprising at least one isotropic diffusion component, wherein each isotropic diffusion component is defined by an isotropic volume ratio and the isotropic diffusivity; and
    iteratively adjusting the isotropic diffusivity and isotropic volume ratio along with at least one anisotropic component of the constant axial diffusivity, the constant radial diffusivity, and one or more of the volume ratios to minimize the difference between the measured diffusion weighted signal and a third diffusion weighted signal estimated using the diffusion basis set;
    wherein the diffusion basis set further comprises the at least one isotropic diffusion component.

3. A method in accordance with claim 1, wherein the detailed composition of the tissue further comprises the volume ratio of each fiber representing anisotropy of diffusion within the volume.

4. A method in accordance with claim 1, wherein the multi-tensor model is a mathematical model.

5. A method in accordance with claim 4, wherein the method further comprises selecting the mathematical model from a plurality of mathematical models based on the magnetic resonance data.

6. A system for determining a diffusivity of each diffusion component of multiple diffusion components within one volume of a plurality of volumes within a tissue using diffusion magnetic resonance data representing the one volume, the system comprising:
    a signal acquisition and processing device configured to receive magnetic resonance data; and
    a processor programmed to:
        determine a quantity of fibers and a primary orientation of each fiber within the one volume by:
            projecting the diffusion magnetic resonance data onto a diffusion basis set comprising a plurality of diffusion bases with a constant axial diffusivity and a constant radial diffusivity, each diffusion basis further defined by a direction;
            iteratively adjusting at least one of the axial diffusivity, the radial diffusivity, and one or more volume ratios to minimize a fitting error between a measured diffusion weighted signal and a diffusion weighted signal estimated using the diffusion basis set; and
            selecting a total number of fibers comprising those diffusion bases with a volume ratio greater than a signal-to-noise threshold and determining the primary orientation of each fiber comprising the direction of each diffusion basis corresponding to each fiber;
        calculate for each fiber a fiber axial diffusivity indicating a diffusion of water in the direction of that fiber and a fiber radial diffusivity indicating a diffusion of water perpendicular to the direction of that fiber by:
            constructing a multi-tensor model comprising the total number of fibers, each fiber characterized by the fiber axial diffusivity, the fiber radial diffusivity, the primary orientation, and the volume ratio of that fiber; and
            iteratively adjusting at least one of the fiber axial diffusivities and the fiber radial diffusivities to minimize a second fitting error between the measured diffusion weighted signal and a second diffusion weighted signal estimated using the diffusion basis set; and determine a detailed composition of the tissue to resolve an underlying tissue pathology, the detailed composition including at least one of the quantity of the fibers, the primary orientation of each fiber, the fiber axial diffusivities, the fiber radial diffusivities, and the fiber volume.

7. A system in accordance with claim 6, wherein the processor is further programmed to calculate at least one isotropic diffusivity by:

defining an isotropic diffusion set comprising at least one isotropic diffusion component, wherein the isotropic diffusion component is defined by an isotropic volume ratio and the isotropic diffusivity; and iteratively adjusting the isotropic diffusivity and isotropic volume ratio along with the at least one anisotropic component of the constant axial diffusivity, the constant radial diffusivity, and one or more of the volume ratios to minimize the difference between the measured diffusion weighted signal and the third diffusion weighted signal estimated using the diffusion basis set;

wherein the diffusion basis set further comprises the at least one isotropic diffusion component.

8. A system in accordance with claim 6, wherein the detailed composition of the tissue further comprises the volume ratio of each fiber representing anisotropy of diffusion within the volume.

9. A system in accordance with claim 6, wherein the multi-tensor model is a mathematical model.

10. A system in accordance with claim 9, wherein the processor is further programmed to select the mathematical model from a plurality of mathematical models based on the magnetic resonance data.

11. One or more non-transitory computer-readable media having computer-executable components, said components comprising:

a signal acquisition and processing component that causes at least one processor to receive diffusion magnetic resonance data; and a computation component for determining a diffusivity of each diffusion component of multiple diffusion components within one volume of a plurality of volumes within a tissue using diffusion magnetic resonance data representing the one volume, the computation component, when executed, causes at least one processor to:

determine a quantity of fibers and a primary orientation of each fiber within the one volume by;

projecting the diffusion magnetic resonance data onto a diffusion basis set comprising a plurality of diffusion bases with a constant axial diffusivity and a constant radial diffusivity, each diffusion basis further defined by a direction;

iteratively adjusting at least one of the axial diffusivity, the radial diffusivity, and one or more volume ratios to minimize a fitting error between a measured diffusion weighted signal and a diffusion weighted signal estimated using the diffusion basis set; and selecting a total number of fibers comprising those diffusion bases with a volume ratio greater than a signal-to-noise threshold and determining the primary orientation of each fiber comprising the direction of each diffusion basis corresponding to each fiber;

calculate for each fiber a fiber axial diffusivity indicating a diffusion of water in the direction of that fiber and a fiber radial diffusivity indicating a diffusion of water perpendicular to the direction of that fiber by:

constructing a multi-tensor model comprising the total number of fibers, each fiber characterized by the fiber axial diffusivity, the fiber radial diffusivity, the primary orientation, and the volume ratio of that fiber; and iteratively adjusting at least one of the fiber axial diffusivities and the fiber radial diffusivities to minimize a second fitting error between the measured diffusion weighted signal and a second diffusion weighted signal estimated using the diffusion basis set; and determine a detailed composition of the tissue to resolve an underlying tissue pathology, the detailed composition including at least one of the fibers, the primary orientation of each fiber, the fiber axial diffusivities, the fiber radial diffusivities, and the fiber volume.

12. One or more non-transitory computer-readable media in accordance with claim 11, wherein the diffusivity component further causes at least one processor to calculate an isotropic diffusivity by:

defining at least one isotropic diffusion basis set comprising at least one isotropic diffusion component, wherein each isotropic diffusion component is defined by an isotropic volume ratio and the isotropic diffusivity; and iteratively adjusting the isotropic diffusivity and isotropic volume ratio along with at least one anisotropic component of the constant axial diffusivity, the constant radial diffusivity, and one or more of the volume ratios to minimize the difference between the measured diffusion weighted signal and a third diffusion weighted signal estimated using the diffusion basis set; and wherein the diffusion basis set further comprises the at least one isotropic diffusion component.

13. One or more non-transitory computer-readable media in accordance with claim 11, wherein the detailed composition of the tissue further comprises the volume ratio of each fiber representing anisotropy of diffusion within the volume.

14. One or more non-transitory computer-readable media in accordance with claim 11, wherein the multi-tensor model is a mathematical model.

\* \* \* \* \*